United States Patent
Okada et al.

(10) Patent No.: US 9,454,091 B2
(45) Date of Patent: Sep. 27, 2016

(54) HYDRAZONE DERIVATIVE OF TRIPHENYLAMINE AND ELECTROPHOTOGRAPHIC PHOTOSENSITIVE MEMBER

(71) Applicant: KYOCERA Document Solutions Inc., Osaka-shi (JP)

(72) Inventors: Hideki Okada, Osaka (JP); Kensuke Kojima, Osaka (JP); Fumio Sugai, Osaka (JP)

(73) Assignee: KYOCERA Document Solutions Inc., Osaka (JP)

( * ) Notice: Subject to any disclaimer, the term of this patent is extended or adjusted under 35 U.S.C. 154(b) by 0 days.

(21) Appl. No.: 14/739,650

(22) Filed: Jun. 15, 2015

(65) Prior Publication Data

US 2015/0378269 A1 Dec. 31, 2015

(30) Foreign Application Priority Data

Jun. 27, 2014 (JP) .................. 2014-133101

(51) Int. Cl.
*G03G 5/06* (2006.01)
*C07C 251/80* (2006.01)
*G03G 5/047* (2006.01)

(52) U.S. Cl.
CPC ........... *G03G 5/0616* (2013.01); *C07C 251/80* (2013.01); *G03G 5/047* (2013.01); *G03G 5/0614* (2013.01)

(58) Field of Classification Search
CPC .......................... G03G 5/0616; C07C 251/80
USPC ..................................... 430/58.45
See application file for complete search history.

(56) References Cited

U.S. PATENT DOCUMENTS

| | | | |
|---|---|---|---|
| 4,278,747 A * | 7/1981 | Murayama ............... | C09B 35/02 430/58.45 |
| 4,465,857 A * | 8/1984 | Neumann ............. | G03G 5/0616 430/58.45 |
| 5,009,976 A * | 4/1991 | Itoh ...................... | G03G 5/0612 430/58.45 |

FOREIGN PATENT DOCUMENTS

| | | | | |
|---|---|---|---|---|
| EP | 0385185 A2 * | 9/1990 | ........... | G03G 5/0612 |
| EP | 0505132 A1 * | 9/1992 | ........... | C07C 251/86 |

(Continued)

OTHER PUBLICATIONS

English language machine translation of JP 4299525 B2 (Jul. 2009).*
English language translation of JP 64-033557 (Feb. 1989).*

*Primary Examiner* — Christopher Rodee
(74) *Attorney, Agent, or Firm* — Studebaker & Brackett PC

(57) ABSTRACT

A hydrazone derivative of triphenylamine is represented by general formula (1).

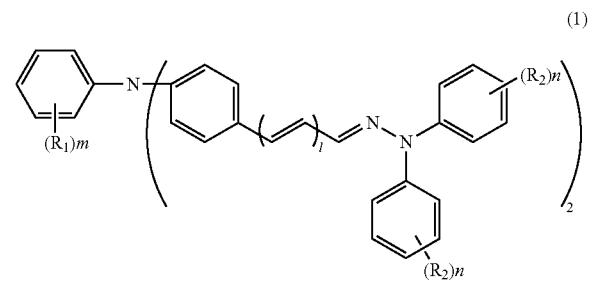

In general formula (1), $R_1$ and $R_2$ each represent, independently of one another, at least one chemical group selected from the group consisting of a halogen atom, an optionally substituted alkyl group having a carbon number of at least 1 and no greater than 6, an optionally substituted alkoxy group having a carbon number of at least 1 and no greater than 6, and an optionally substituted aryl group having a carbon number of at least 6 and no greater than 12. In general formula (1), m and n each represent, independently of one another, an integer of at least 0 and no greater than 4. In general formula (1), l represents 0 or 1.

7 Claims, 6 Drawing Sheets

(56) References Cited

FOREIGN PATENT DOCUMENTS

| JP | 63206758 | A | * | 8/1988 |
| JP | 64033557 | A | * | 2/1989 |
| JP | 2007-223923 | A | | 9/2007 |
| JP | 4299525 | B2 | * | 7/2009 |

* cited by examiner

HYDRAZONE DERIVATIVE OF TRIPHENYLAMINE AND ELECTROPHOTOGRAPHIC PHOTOSENSITIVE MEMBER

INCORPORATION BY REFERENCE

The present application claims priority under 35 U.S.C. §119 to Japanese Patent Application No. 2014-133101, filed Jun. 27, 2014. The contents of this application are incorporated herein by reference in their entirety.

BACKGROUND

The present disclosure relates to hydrazone derivatives of triphenylamine and electrophotographic photosensitive members.

Electrophotographic photosensitive members are used as image bearing members in electrophotographic printers and multifunction peripherals. A typical electrophotographic photosensitive member includes a conductive substrate and a photosensitive layer located either directly or indirectly on the conductive substrate. A photosensitive member including a photosensitive layer that contains a charge generating material, a charge transport material, and resin for binding the aforementioned materials is referred to as an organic electrophotographic photosensitive member. Among such organic electrophotographic photosensitive members, photosensitive members in which a charge transport function and a charge generation function are implemented by separate layers are referred to as multi-layer electrophotographic photosensitive members. On the other hand, photosensitive members in which a charge transport material and a charge generating material are contained in the same single layer, and thus in which a charge transport function and a charge generation function are both implemented by the single layer, are referred to as single-layer electrophotographic photosensitive members.

Triphenylamine derivatives are commonly known to be usable as charge transport materials in organic electrophotographic photosensitive members.

SUMMARY

A hydrazone derivative of triphenylamine according to the present disclosure is represented by general formula (1).

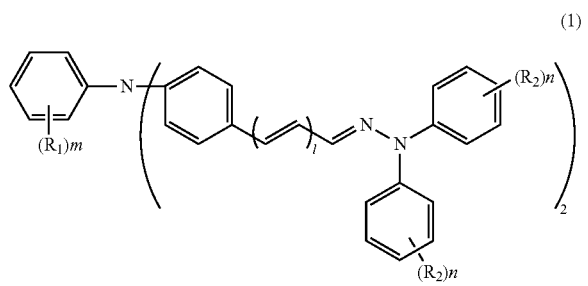

(1)

In general formula (1), $R_1$ and $R_2$ each represent, independently of one another, at least one chemical group selected from the group consisting of a halogen atom, an optionally substituted alkyl group having a carbon number of at least 1 and no greater than 6, an optionally substituted alkoxy group having a carbon number of at least 1 and no greater than 6, and an optionally substituted aryl group having a carbon number of at least 6 and no greater than 12. In general formula (1), m and n each represent, independently of one another, an integer of at least 0 and no greater than 4. In general formula (1), l represents 0 or 1.

An electrophotographic photosensitive member according to the present disclosure includes a photosensitive layer containing a charge generating material, a charge transport material, and a binder resin. The photosensitive layer is either a multi-layer photosensitive layer or a single-layer photosensitive layer. The multi-layer photosensitive layer includes a charge generating layer that contains the charge generating material and a charge transport layer that contains the charge transport material and the binder resin. In the multi-layer photosensitive layer, the charge generating layer and the charge transport layer are stacked with the charge transport layer as an uppermost layer. The single-layer photosensitive layer contains the charge generating material, the charge transport material, and the binder resin. The charge transport material contained in the photosensitive layer is the hydrazone derivative of triphenylamine described above. In a situation in which the photosensitive layer contains both a hole transport material and an electron transport material as charge transport materials, the photosensitive layer preferably contains the hydrazone derivative of triphenylamine described above as the hole transport material.

DETAILED DESCRIPTION

Figure 1:
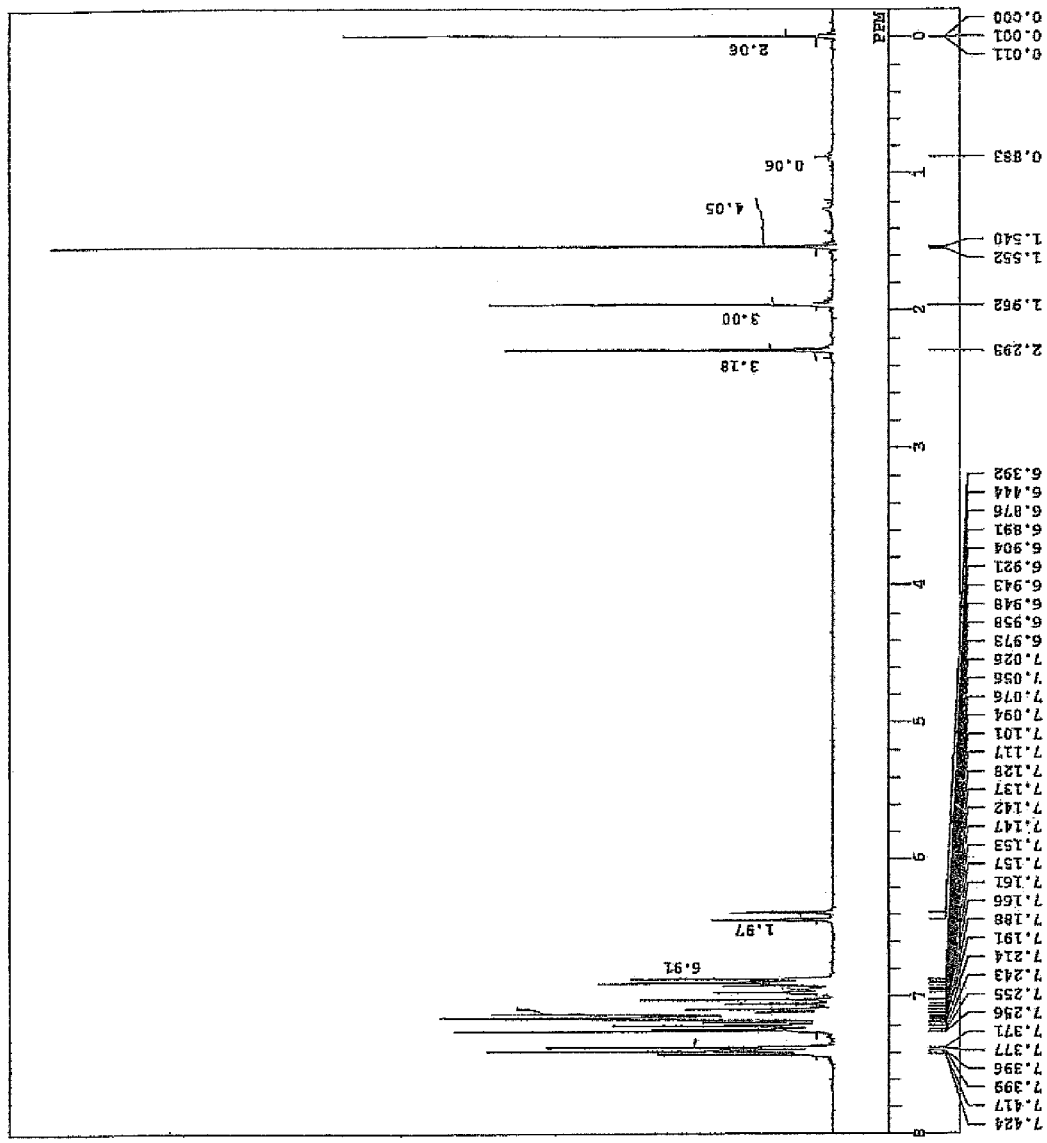
FIG. 1 is a $^1$H-NMR spectral chart for a hydrazone derivative of triphenylamine represented by formula (HT-1).

The following explains an embodiment of the present disclosure in detail. The present disclosure is of course not in any way limited by the following embodiment and appropriate alterations may be made in practice within the intended scope of the present disclosure.

[Hydrazone Derivative of Triphenylamine]

The following explains a hydrazone derivative of triphenylamine according to the present embodiment. The hydrazone derivative of triphenylamine according to the present embodiment is represented by general formula (1) shown below.

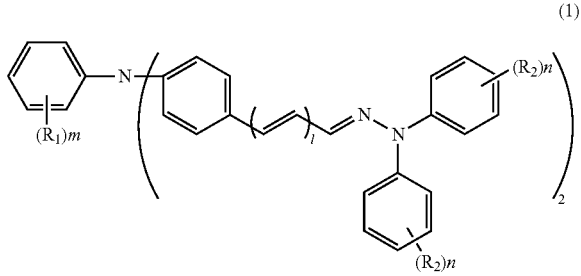

(1)

In general formula (1), $R_1$ and $R_2$ each represent, independently of one another, at least one chemical group selected from the group consisting of a halogen atom, an optionally substituted alkyl group having a carbon number of at least 1 and no greater than 6, an optionally substituted alkoxy group having a carbon number of at least 1 and no greater than 6, and an optionally substituted aryl group having a carbon number of at least 6 and no greater than 12. In general formula (1), m and n each represent, independently of one another, an integer of at least 0 and no greater than 4. In general formula (1), l represents 0 or 1.

In the hydrazone derivative of triphenylamine represented by general formula (1) shown above, two hydrazone parts are located symmetrically relative to a nitrogen atom of a triphenylamine part. A double bond is present between the triphenylamine part and each of the hydrazone parts. The hydrazone derivative of triphenylamine having the structure described above tends to have excellent properties in terms of solvent solubility and resin compatibility. When the hydrazone derivative of triphenylamine having the structure described above is contained in a photosensitive member, the photosensitive member tends to have excellent surface appearance. The above effect is thought to be due to the fact that crystallization of the hydrazone derivative of triphenylamine in the photosensitive layer can be inhibited during formation of a film of the photosensitive layer. Furthermore, the hydrazone derivative of triphenylamine represented by general formula (1) can be easily dispersed in the photosensitive layer in a uniform manner. Uniform dispersion of the hydrazone derivative of triphenylamine in the photosensitive layer increases the likelihood of the photosensitive layer exhibiting excellent electrical properties. By using a photosensitive member having excellent electrical properties and surface appearance in image formation, high quality image formation can be achieved over an extended period of time.

In order to provide a photosensitive member having excellent electrical properties and surface appearance, in the hydrazone derivative of triphenylamine represented by general formula (1), it is particularly preferable that $R_1$ and $R_2$ each represent, independently of one another, an alkyl group having a carbon number of at least 1 and no greater than 6 or an alkoxy group having a carbon number of at least 1 and no greater than 6.

In order to provide a photosensitive member with excellent electrical properties and surface appearance, in the hydrazone derivative of triphenylamine represented by general formula (1), it is particularly preferable that m and n each represent, independently of one another, an integer of at least 0 and no greater than 2.

In order to provide a photosensitive member having excellent electrical properties and surface appearance, it is particularly preferable that a halogen atom in general formula (1) is a fluorine atom, a chlorine atom, or a bromine atom.

In order to provide a photosensitive member having excellent electrical properties and surface appearance, it is particularly preferable that the alkyl group having a carbon number of at least 1 and no greater than 6 in general formula (1) is a methyl group, an ethyl group, a propyl, an isopropyl group, an n-butyl group, a t-butyl group, a pentyl group, an isopentyl group, a neopentyl group, or a hexyl group.

In order to provide a photosensitive member having excellent electrical properties and surface appearance, it is particularly preferable that the alkoxy group having a carbon number of at least 1 and no greater than 6 in general formula (1) is an ethoxy group, an n-propoxy group, an isopropoxy group, an n-butoxy group, an s-butoxy group, a t-butoxy group, a pentyloxy group, an isopentyloxy group, a neopentyloxy group, or a hexyloxy group.

In order to provide a photosensitive member having excellent electrical properties and surface appearance, it is particularly preferable that the aryl group having a carbon number of at least 6 and no greater than 12 in general formula (1) is a phenyl group, a tolyl group, a xylyl group, a mesityl group, a naphthyl group, an anthryl group, or a phenanthryl group.

One or more of the alkyl group, the alkoxy group, and the aryl group in general formula (1) may have a substituent. Substituents of the aforementioned chemical groups in general formula (1) may be selected as appropriate, in accordance with an intended use of the photosensitive member, from the group consisting of a halogen atom (specific examples include a fluoro group, a chloro group, a bromo group, and an iodo group), a nitro group, a cyano group, an amino group, a hydroxyl group, a carboxyl group, a sulfanyl group, a carbamoyl group, a straight-chain or branched alkyl group having a carbon number of at least 1 and no greater than 12, a cycloalkyl group having a carbon number of at least 3 and no greater than 12, an alkoxy group having a carbon number of at least 1 and no greater than 12, an alkylsulfanyl group having a carbon number of at least 1 and no greater than 12, an alkylsulfonyl group having a carbon number of at least 1 and no greater than 12, an alkanoyl group having a carbon number of at least 2 and no greater than 13, an alkoxycarbonyl group having a carbon number of at least 2 and no greater than 13, an aryl group having a carbon number of at least 6 and no greater than 14 (mono-cyclic, fused bi-cyclic, or fused tri-cyclic), and a heterocyclic group having at least 6 and no greater than 14 ring members (mono-cyclic, fused bi-cyclic, or fused tri-cyclic). In a structure including a plurality of substituents (i.e., in which there is substitution at a plurality of locations), the substituents may be of the same type or of different types.

Specific examples of the hydrazone derivative of triphenylamine represented by general formula (1) are indicated by formulae (HT-1) to (HT-7) shown below.

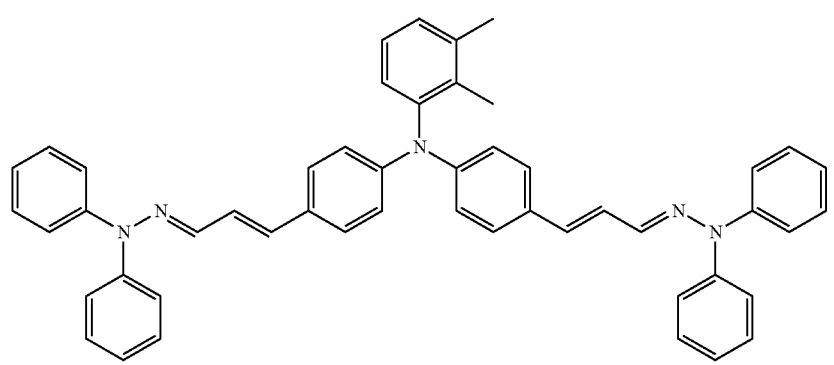
(HT-1)
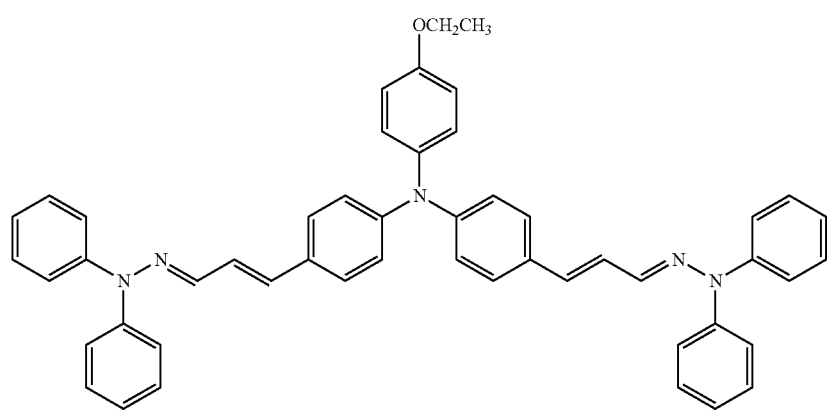
(HT-2)
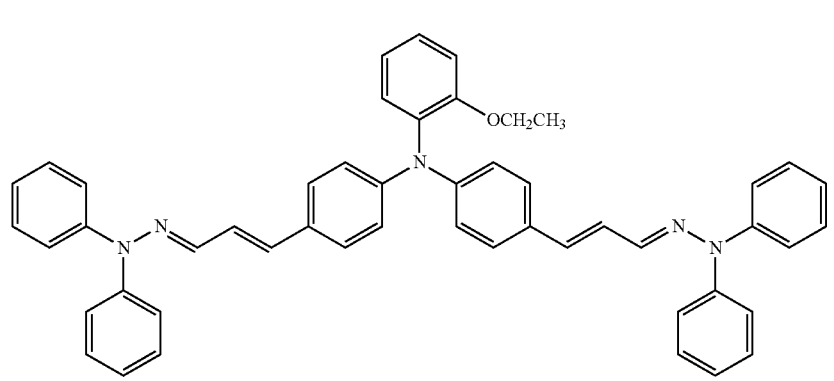
(HT-3)
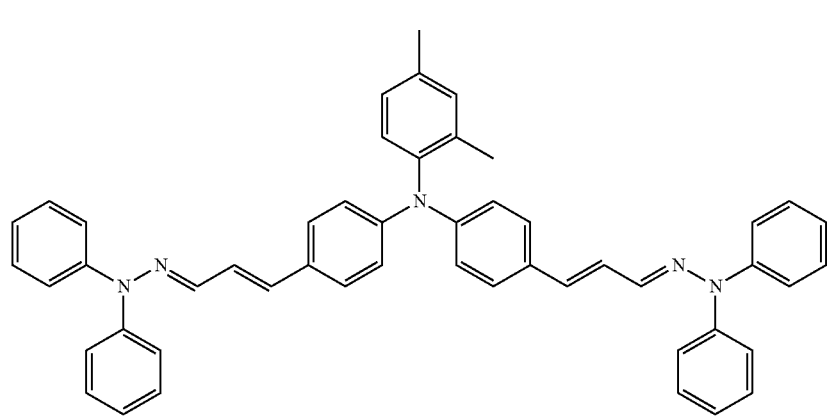
(HT-4)

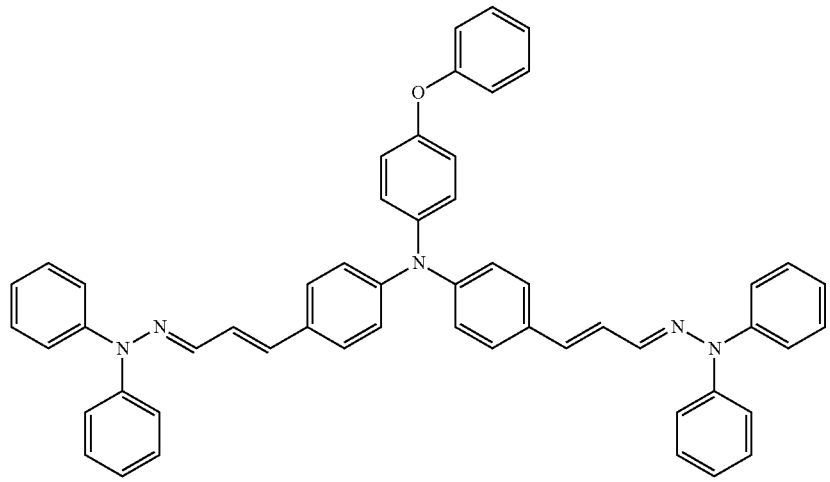

(HT-5)

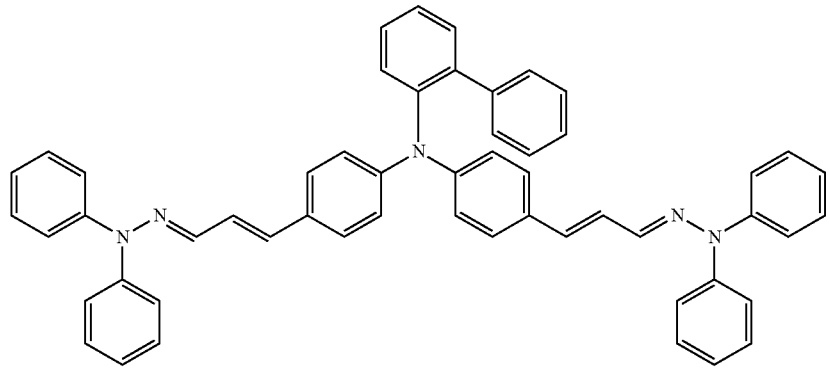

(HT-6)

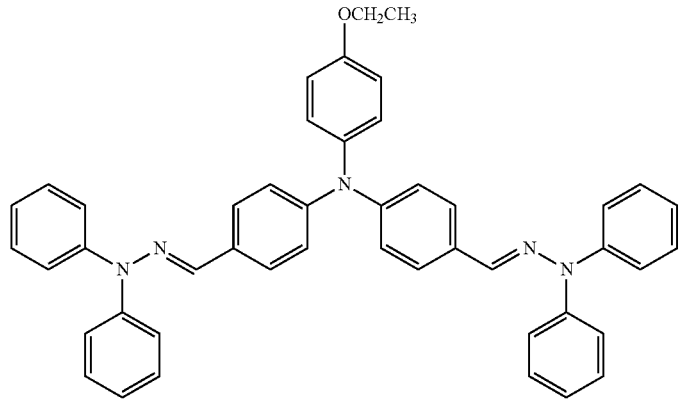

(HT-7)

In order to provide a photosensitive member having excellent electrical properties and surface appearance, the hydrazone derivatives of triphenylamine represented by formulae (HT-1) to (HT-7) are preferable, with the hydrazone derivatives of triphenylamine represented by formulae (HT-1) to (HT-4) being particularly preferable. FIGS. 1-4 are $^1$H-NMR spectra for the hydrazone derivatives of triphenylamine represented by formulae (HT-1) to (HT-4) respectively. Formulae (HT-1) and (HT-4) are formulae for which, in general formula (1), $R_1$ represents a methyl group, m represents 2, n represents 0, and 1 represents 1. Among the two chemical groups $R_1$ (methyl groups) in formula (HT-1), one chemical group $R_1$ (methyl group) is at an ortho substitution position and the other chemical group $R_1$ (methyl group) is at a meta substitution position. Among the two chemical groups $R_1$ (methyl groups) in formula (HT-4), one chemical group $R_1$ (methyl group) is at an ortho substitution position and the other chemical group $R_1$ (methyl group) is at a para substitution position. Formulae (HT-2) and (HT-3) are formulae for which, in general formula (1), $R_1$ represents an ethoxy group, m represents 1, n represents 0, and 1 represents 1. The chemical group $R_1$ (ethoxy group) in formula (HT-2) is at a para substitution position. The chemical group $R_1$ (ethoxy group) in formula (HT-3) is at an ortho substitution position. Formula (HT-5) is a formula for which, in general formula (1), $R_1$ represents a phenoxy group, m represents 1, n represents 0, and 1 represents 1. Formula (HT-6) is a formula for which, in general formula (1), $R_1$ represents a phenyl group, m represents 1, n represents 0, and 1 represents 1. Formula (HT-7) is a formula for which, in general formula (1), $R_1$ represents an ethoxy group, m represents 1, n represents 0, and 1 represents 0.

The hydrazone derivative of triphenylamine represented by general formula (1) shown above can for example be produced through a production method including reactions represented by chemical equations (R-1), (R-2), and (R-3) shown below.

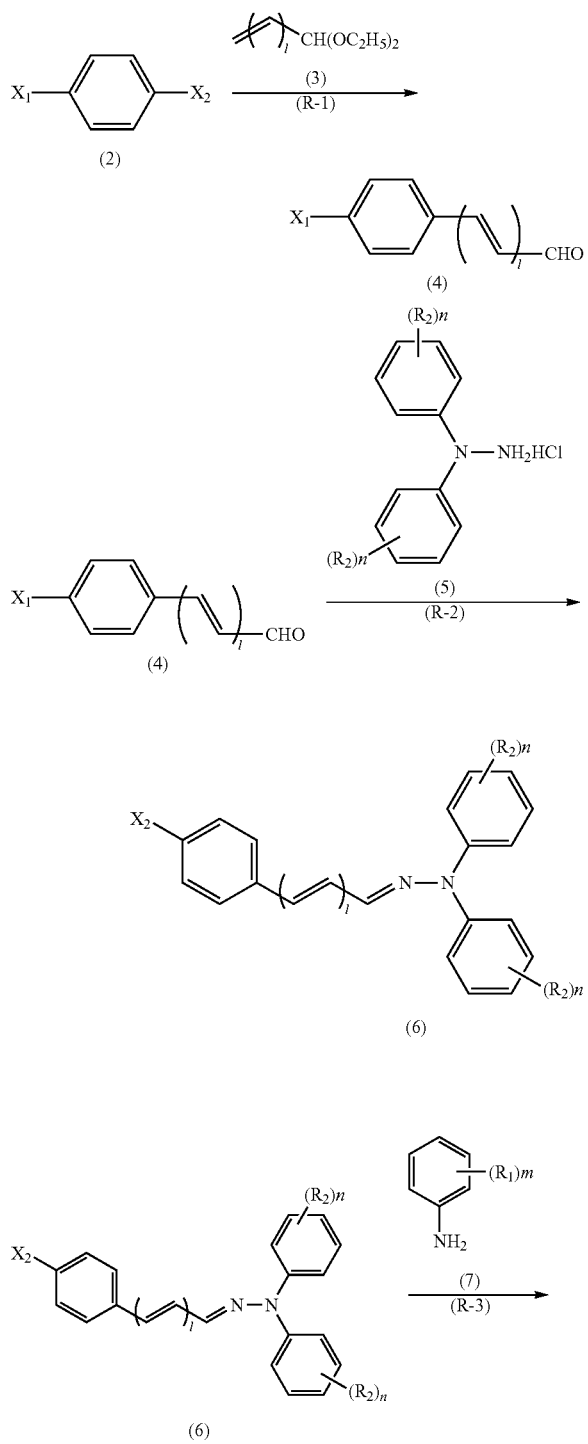

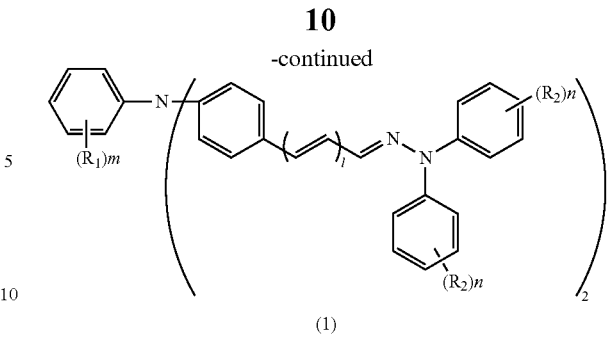

(1)

In chemical equations (R-1), (R-2), and (R-3), $R_1$ and $R_2$ each represent, independently of one another, at least one chemical group selected from the group consisting of a halogen atom, an optionally substituted alkyl group having a carbon number of at least 1 and no greater than 6, an optionally substituted alkoxy group having a carbon number of at least 1 and no greater than 6, and an optionally substituted aryl group having a carbon number of at least 6 and no greater than 12. In the chemical equations (R-1), (R-2), and (R-3), m and n each represent, independently of one another, an integer of at least 0 and no greater than 4. In the chemical equations (R-1), (R-2), and (R-3), 1 represents 0 or 1. $X_1$ and $X_2$ each represent, independently of one another, a halogen atom. In the following explanation, the reactions shown by the above chemical equations may be referred to by the names of the equations. For example, the reaction shown by chemical equation (R-1) may be referred to as reaction (R-1).

The following describes reaction (R-1).

In reaction (R-1), a compound represented by general formula (2) is caused to react with a compound represented by general formula (3) to yield a compound represented by general formula (4). Reaction (R-1) is for example carried out in the presence of a catalyst or base in a solvent having the materials dissolved therein. The compound represented by general formula (4) is obtained by performing extraction and purification on the reaction product.

A reaction ratio of the compound represented by general formula (2) and the compound represented by general formula (3) is preferably a molar ratio of 1:1 to 1:4 (compound represented by general formula (2): compound represented by general formula (3)). If the amount of the compound represented by general formula (2) is too small, there is a reduction in the yield of the compound represented by general formula (4). On the other hand, if the amount of the compound represented by general formula (2) is too large, purification of the compound represented by general formula (4) becomes more difficult due to a large amount of the compound represented by general formula (2) remaining unreacted.

In order to carry out reaction (R-1) efficiently and appropriately using relatively simple production equipment, reaction (R-1) preferably has a reaction temperature of at least 70° C. and no greater than 120° C., and a reaction time of at least 2 hours and no greater than 6 hours.

A palladium compound is preferably used as a catalyst in reaction (R-1). Use of the palladium compound as the catalyst enables reduction of the activation energy of reaction (R-1). By reducing the activation energy of reaction (R-1), the yield of the compound represented by general formula (4) can be improved.

Preferable examples of palladium compounds that can be used in reaction (R-1) include tetravalent palladium compounds (specific examples include hexachloro palladium (IV) sodium tetrahydrate and hexachloro palladium(IV) potassium tetrahydrate), divalent palladium compounds (specific examples include palladium(II) chloride, palladium (II) bromide, palladium(II) acetate, palladium(II) acetylacetate, dichlorobis(benzonitrile)palladium(II), dichlorobis (triphenylphosphine)palladium(II), dichlorotetramine palladium(II), and dichloro(cycloocta-1,5-diene)palladium (II)), and other palladium compounds (specific examples include tris(dibenzylideneacetone)dipalladium(0), tris (dibenzylideneacetone)dipalladium(0) chloroform complex, and tetrakis(triphenylphosphine)palladium(0)). Any one of the palladium compounds listed above may be used or a combination of any two or more of the palladium compounds listed above may be used.

Reaction (R-1) can for example be carried out in the presence of a base. It is thought that by carrying out reaction (R-1) in the presence of a base, hydrogen halide produced during the reaction is quickly neutralized and catalyst performance is improved. Improved catalyst performance leads to improved yield of the compound represented by general formula (4).

The base used in reaction (R-1) may be an inorganic base or an organic base. Preferable organic bases for example include alkali metal alkoxides (specific examples include sodium methoxide, sodium ethoxide, potassium methoxide, potassium ethoxide, lithium tert-butoxide, sodium tert-butoxide, and potassium tert-butoxide), with sodium tert-butoxide being particularly preferable. Preferable inorganic bases include potassium carbonate, tripotassium phosphate, and cesium fluoride.

Reaction (R-1) can for example be carried out in a solvent. Preferable solvents for example include xylene (any of o-, m-, and p-xylene), toluene, tetrahydrofuran, and N,N-dimethylformamide.

The following describes reaction (R-2).

In reaction (R-2), the compound represented by general formula (4) is caused to react (dehydration reaction) with a compound represented by general formula (5) to yield a compound represented by general formula (6). The compound represented by general formula (6) is obtained by performing extraction and purification on the reaction product.

A reaction ratio of the compound represented by general formula (4) and the compound represented by general formula (5) is preferably a molar ratio of 1:1 to 1:2.5 (compound represented by general formula (4): compound represented by general formula (5)). If the amount of the compound represented by general formula (4) is too small, there is a reduction in the yield of the compound represented by general formula (6). On the other hand, if the amount of the compound represented by general formula (4) is too large, purification of the compound represented by general formula (6) becomes more difficult due to a large amount of the compound represented by general formula (4) remaining unreacted.

In order to carry out reaction (R-2) efficiently and appropriately using relatively simple production equipment, reaction (R-2) preferably has a reaction temperature of at least 80° C. and no greater than 140° C., and a reaction time of at least 2 hours and no greater than 10 hours.

Reaction (R-2) can for example be carried out in the presence of a catalyst. Preferable examples of catalysts that can be used in reaction (R-2) include p-toluenesulfonic acid, concentrated sulfuric acid, and hydrochloric acid.

Reaction (R-2) can for example be carried out in a solvent. Preferable examples of solvents that can be used in reaction (R-2) include toluene, xylene, methanol, ethanol, tetrahydrofuran, and N,N-dimethylformamide.

The following describes reaction (R-3).

Reaction (R-3) is for example carried out in the presence of a catalyst in a solvent by causing the compound represented by general formula (6) to react (coupling reaction) with a compound represented by general formula (7) to yield the hydrazone derivative of triphenylamine represented by general formula (1). The hydrazone derivative of triphenylamine represented by general formula (1) is obtained by performing extraction and purification on the reaction product.

A reaction ratio of the compound represented by general formula (6) and the compound represented by general formula (7) is preferably a molar ratio of 2:1 to 2.5:1 (compound represented by general formula (6): compound represented by general formula (7)). If the amount of the compound represented by general formula (6) is too small, there is a reduction in the yield of the hydrazone derivative of triphenylamine represented by general formula (1). On the other hand, if the amount of the compound represented by general formula (6) is too large, purification of the hydrazone derivative of triphenylamine represented by general formula (1) becomes more difficult due to a large amount of the compound represented by general formula (6) remaining unreacted.

In order to carry out reaction (R-3) efficiently and appropriately using relatively simple production equipment, reaction (R-3) preferably has a reaction temperature of at least 80° C. and no greater than 140° C., and a reaction time of at least 2 hours and no greater than 10 hours.

A palladium compound is preferably used as a catalyst in reaction (R-3). Use of the palladium compound as the catalyst enables a reduction in the activation energy of reaction (R-3). By reducing the activation energy of reaction (R-3), the yield of the hydrazone derivative of triphenylamine represented by general formula (1) can be improved.

Preferable examples of palladium compounds that can be used in reaction (R-3) include tetravalent palladium compounds (specific examples include hexachloro palladium (IV) sodium tetrahydrate and hexachloro palladium(IV) potassium tetrahydrate), divalent palladium compounds (specific examples include palladium(II) chloride, palladium (II) bromide, palladium(II) acetate, palladium(II) acetylacetate, dichlorobis(benzonitrile)palladium(II), dichlorobis (triphenylphosphine)palladium(II), dichlorotetramine palladium(II), and dichloro(cycloocta-1,5-diene)palladium (II)), and other palladium compounds (specific examples include tris(dibenzylideneacetone)dipalladium(0), tris (dibenzylideneacetone)dipalladium(0) chloroform complex, and tetrakis(triphenylphosphine)palladium(0)). Any one of the palladium compounds listed above may be used or a combination of any two or more of the palladium compounds listed above may be used.

Reaction (R-3) can be carried out in a solvent. Examples of preferable solvents include xylene, toluene, tetrahydrofuran, and dimethyl formamide.

The production method according to the present embodiment may, depending on necessity thereof, include other processes in addition to processes of carrying out reactions (R-1), (R-2), and (R-3).

[Photosensitive Member]

The following explains a photosensitive member according to the present embodiment. The photosensitive member according to the present embodiment is an electrophotographic photosensitive member. The photosensitive member according to the present embodiment includes a photosensitive layer. The photosensitive layer contains a charge generating material, a charge transport material, and a resin.

The photosensitive member according to the present embodiment may be a multi-layer photosensitive member such as described below or a single-layer photosensitive member such as described below. In the following explanation, a photosensitive layer of a multi-layer photosensitive member is referred to as a multi-layer photosensitive layer. Also, a photosensitive layer of a single-layer photosensitive member is referred to as a single-layer photosensitive layer. A resin contained in a charge transport layer of a multi-layer photosensitive member and a resin contained in a single-layer photosensitive layer may each be referred to as a binder resin. In a situation in which a charge generating layer of a multi-layer photosensitive member contains a resin (charge generating layer binder resin), the resin contained in the charge generating layer may be referred to as a base resin.

A multi-layer photosensitive member includes a multi-layer photosensitive layer. The multi-layer photosensitive layer includes a charge generating layer and a charge transport layer. The charge transport layer is located at an upper surface of the multi-layer photosensitive layer. The charge generating layer contains a charge generating material. The charge transport layer contains a charge transport material and a binder resin.

A single-layer photosensitive member includes a single-layer photosensitive layer. The single-layer photosensitive layer is a single layer containing a charge generating material, a charge transport material, and a binder resin.

[Multi-Layer Photosensitive Member]

Figure 5A:
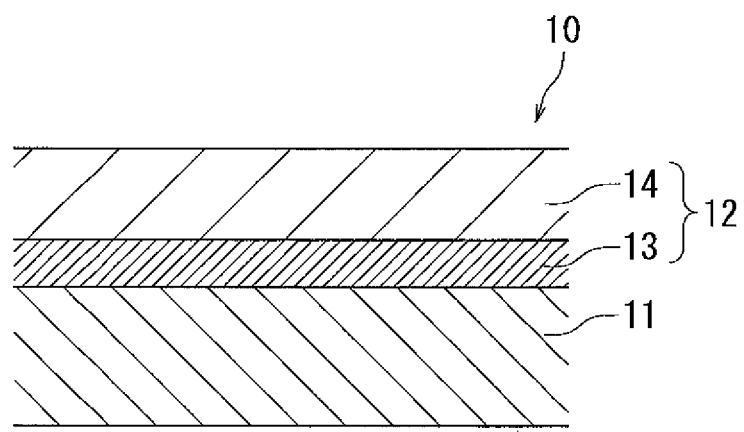
FIGS. 5A and 5B are each a rough cross-sectional illustration of structure of a multi-layer electrophotographic photosensitive member according to an embodiment of the present disclosure.
Figure 5B:
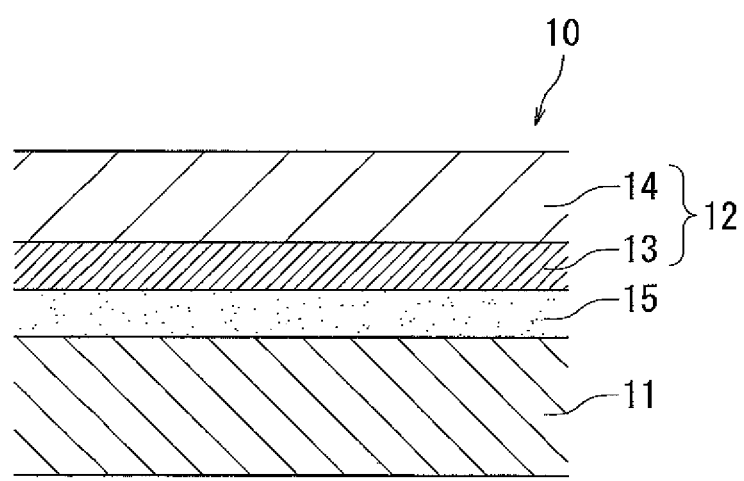

The following explains the multi-layer photosensitive member with reference to FIGS. 5A and 5B. As illustrated in FIG. 5A, a multi-layer photosensitive member 10 includes a substrate 11 and a multi-layer photosensitive layer 12. The multi-layer photosensitive layer 12 includes a charge generating layer 13 and a charge transport layer 14. The charge generating layer 13 contains a charge generating material. The charge transport layer 14 contains a charge transport material and a binder resin. In the multi-layer photosensitive member 10 illustrated in FIG. 5A, the charge generating layer 13 and the charge transport layer 14 are stacked on the substrate 11 in stated order with the charge transport layer 14 at an upper surface. Through a configuration in which the charge transport layer 14 is located at the upper surface, photosensitive member abrasion resistance can be improved while also maintaining excellent photosensitive member electrical properties. However, the multi-layer photosensitive member is not limited to having the structure illustrated in FIG. 5A. For example, an intermediate layer 15 may be present between the substrate 11 and the multi-layer photosensitive layer 12 as illustrated in FIG. 5B.

In order to improve electrical properties of the photosensitive member, the charge generating layer preferably has a thickness of at least 0.01 µm and no greater than 5 µm, and more preferably at least 0.1 µm and no greater than 3 µm. In order to improve electrical properties of the photosensitive member, the charge transport layer preferably has a thickness of at least 2 µm and no greater than 100 µm, and more preferably at least 5 µm and no greater than 50 µm.

[Single-Layer Photosensitive Member]

Figure 6A:
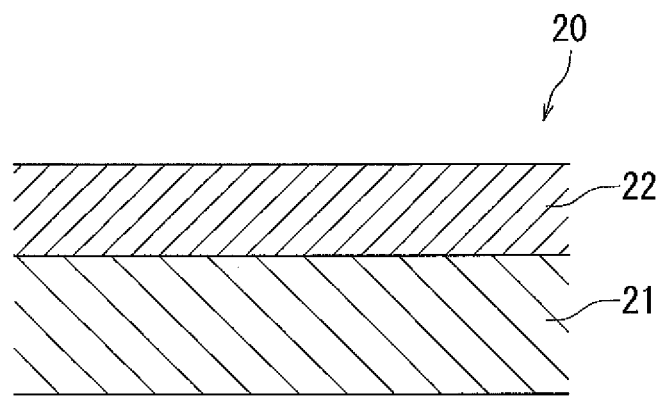
FIGS. 6A and 6B are each a rough cross-sectional illustration of structure of a single-layer electrophotographic photosensitive member according to an embodiment of the present disclosure.
Figure 6B:
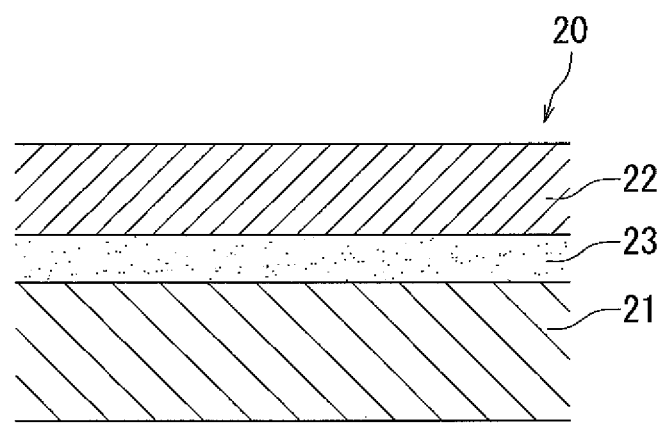

The following explains the single-layer photosensitive member with reference to FIGS. 6A and 6B. As illustrated in FIG. 6A, a single-layer photosensitive member 20 includes a substrate 21 and a single-layer photosensitive layer 22. The single-layer photosensitive layer 22 is located on the substrate 21. The single-layer photosensitive layer 22 contains a charge generating material, a charge transport material (more specifically, a hole transport material that transports charge in the form of holes and an electron transport material that transports charge in the form of electrons), and a binder resin. The single-layer photosensitive layer 22 may be located directly on the substrate 21 as illustrated in FIG. 6A. Alternatively, an intermediate layer 23 may be present between the substrate 21 and the single-layer photosensitive layer 22 as illustrated in FIG. 6B.

In order to improve electrical properties of the photosensitive member, the single-layer photosensitive layer 22 preferably has a thickness of at least 5 µm and no greater than 100 µm, and more preferably at least 10 µm and no greater than 50 µm.

In the photosensitive member according to the present embodiment (for example, the single-layer photosensitive member or the multi-layer photosensitive member), the photosensitive layer (for example, the single-layer photosensitive layer or the multi-layer photosensitive layer) is preferably an outermost layer in order to prevent image deletion and limit production costs.

[Common Elements of Configuration]

The following explains elements of configuration that are common to both the single-layer photosensitive member and the multi-layer photosensitive member. Note that in the present description the term "-based" may be appended to the name of a chemical compound in order to form a generic name encompassing both the chemical compound itself and derivatives thereof. Also, when the term "-based" is appended to the name of a chemical compound used in the name of a polymer, the term indicates that a repeating unit of the polymer originates from the chemical compound or a derivative thereof.

[Substrate]

The multi-layer photosensitive member and the single-layer photosensitive member each include a substrate (for example, the substrate 11 shown in FIGS. 5A and 5B or the substrate 21 shown in FIGS. 6A and 6B). The substrate may have any appropriate shape. For example, the substrate may sheet-shaped or drum-shaped. Preferably at least a surface portion of the substrate is conductive. The entire substrate may be made from a conductive material. Alternatively, the surface of an insulting material (specific examples include plastic materials and glass) may be coated with a conductive material through a process such as vapor deposition. Examples of preferable conductive materials include metals such as aluminum, iron, copper, tin, platinum, silver, vanadium, molybdenum, chromium, cadmium, titanium, nickel, palladium, indium, stainless steel, and brass, and alloys of the aforementioned metals. Any one of the conductive materials listed above may be used or a combination of any two or more of the conductive materials listed above may be used.

In order to increase movement of charge from the photosensitive layer to the substrate, it is preferable that the substrate is substantially made from aluminum or an aluminum alloy. It is easier to form an image with high image quality when the photosensitive member used in image formation has high movement of charge from the photosensitive layer to the substrate.

[Charge Generating Material]

The charge generating layer of the multi-layer photosensitive member (for example, the charge generating layer 13 shown in FIGS. 5A and 5B) and the single-layer photosensitive layer of the single-layer photosensitive member (for example, the single-layer photosensitive layer 22 shown in FIGS. 6A and 6B) each contain a charge generating material.

Examples of preferable charge generating materials include X-form metal-free phthalocyanine (x-$H_2$Pc), Y-form titanyl phthalocyanine (Y-TiOPc), perylene pigments, bisazo pigments, dithioketopyrrolopyrrole pigments, metal-free naphthalocyanine pigments, metal naphthalocyanine pigments, squaraine pigments, tris-azo pigments, indigo pigments, azulenium pigments, cyanine pigments, powders of inorganic photoconductive materials such as selenium, selenium-tellurium, selenium-arsenic, cadmium sulfide, and amorphous silicon, pyrylium salts, anthanthrone-based pigments, triphenylmethane-based pigments, threne-based pigments, toluidine-based pigments, pyrazoline-based pigments, and quinacridone-based pigments.

In a digital optical image forming apparatus (for example, a laser beam printer or facsimile machine) in which a semiconductor laser light source having a wavelength of 700 nm or greater is used, a photosensitive member that is sensitive to a range of wavelengths of greater than or equal to 700 nm is preferably used. The photosensitive member that is sensitive to a range of wavelengths of greater than or equal to 700 nm preferably includes a phthalocyanine-based pigment as a charge generating material, and particularly preferably include X-form metal-free phthalocyanine (x-$H_2$Pc) or Y-form titanyl phthalocyanine (Y-TiOPc) as a charge generating material. Also, in an image forming apparatus in which a short-wavelength laser light source having a wavelength of at least 350 nm and no greater than 550 nm is used, a photosensitive member having an anthanthrone-based pigment or a perylene-based pigment as a charge generating material is preferably used.

The amount of the charge generating material in the multi-layer photosensitive member is preferably at least 5 parts by mass and no greater than 1,000 parts by mass relative to 100 parts by mass of the base resin, and more preferably at least 30 parts by mass and no greater than 500 parts by mass.

The amount of the charge generating material in the single-layer photosensitive member is preferably at least 0.1 parts by mass and no greater than 50 parts by mass relative to 100 parts by mass of the binder resin, and more preferably at least 0.5 parts by mass and no greater than 30 parts by mass.

[Charge Transport Material]

The charge transport layer of the multi-layer photosensitive member (for example, the charge transport layer 14 shown in FIGS. 5A and 5B) and the single-layer photosensitive layer of the single-layer photosensitive member (for example, the single-layer photosensitive layer 22 shown in FIGS. 6A and 6B) each contain a charge transport material. The photosensitive member according to the present embodiment contains the hydrazone derivative of triphenylamine represented by general formula (1) as the charge transport material. The hydrazone derivative of triphenylamine represented by general formula (1) functions as a hole transport material.

In the multi-layer photosensitive member, the amount of the hydrazone derivative of triphenylamine represented by general formula (1) is preferably at least 10 parts by mass and no greater than 200 parts by mass relative to 100 parts by mass of the binder resin, and more preferably at least 20 parts by mass and no greater than 100 parts by mass.

In the single-layer photosensitive member, the amount of the hydrazone derivative of triphenylamine represented by general formula (1) is preferably at least 10 parts by mass and no greater than 200 parts by mass relative to 100 parts by mass of the binder resin, and more preferably at least 10 parts by mass and no greater than 100 parts by mass.

The charge transport layer of the multi-layer photosensitive member and the single-layer photosensitive layer of the single-layer photosensitive member may optionally contain an electron transport material in addition to the hole transport material.

In a situation in which an electron transport material is used in combination with a hole transport material, the electron transport material may not transport electrons if there is only a small amount of the electron transport material present. In an example in which the charge generating layer 13 of the multi-layer photosensitive member 10 illustrated in FIG. 5A is extremely thin, all electrons generated in the charge generating layer 13 can easily move into the substrate 11 (conductive substrate). Therefore, only holes generated in the charge generating layer 13 are transported through the charge transport layer 14 by the hole transport material. The electron transport material supplements the hole transport material in the charge transport layer 14 by contributing to charge (hole) transport. In the following explanation, an electron transport material such as described above that indirectly contributes to charge (hole) transport without directly transporting charge (holes) is referred to as an electron acceptor compound.

In contrast, in the single-layer photosensitive member 20 illustrated in FIG. 6A or 6B, holes and electrons are generated over a wide range from a surface of the single-layer photosensitive layer 22 to an internal part (bulk) of the single-layer photosensitive layer 22. In the single-layer photosensitive layer 22, among the charge transport materials, the hole transport material transports holes and the electron transport material transports electrons.

Examples of preferable electron transport materials include quinone-based compounds (specific examples include naphthoquinone-based compounds, diphenoquinone-based compounds, anthraquinone-based compounds, azoquinone-based compounds, nitroanthraquinone-based compounds, and dinitroanthraquinone-based compounds), malononitrile-based compounds, thiopyran-based compounds, trinitrothioxanthone-based compounds, 3,4,5,7-tetranitro-9-fluorenone-based compounds, dinitroanthracene-based compounds, dinitroacridine-based compounds, tetracyanoethylene, 2,4,8-trinitrothioxanthone, dinitrobenzene, dinitroanthracene, dinitroacridine, succinic anhydride, maleic anhydride, and dibromomaleic anhydride. Any one of the electron transport materials listed above may be used or a combination of any two or more of the electron transport materials listed above may be used.

In the multi-layer photosensitive member, the amount of the charge transport material is preferably at least 0.1 parts by mass and no greater than 20 parts by mass relative to 100 parts by mass of the binder resin, and more preferably at least 0.5 parts by mass and no greater than 10 parts by mass.

In the single-layer photosensitive member, the amount of the electron transport material is preferably at least 5 parts by mass and no greater than 100 parts by mass relative to 100 parts by mass of the binder resin, and more preferably at least 10 parts by mass and no greater than 80 parts by mass.

[Resin]

The charge transport layer of the multi-layer photosensitive member and the single-layer photosensitive layer of the single-layer photosensitive member each contain a resin (binder resin). The charge generating layer of the multi-layer photosensitive member may optionally contain a resin (base resin).

(Base Resin)

In the multi-layer photosensitive member, the base resin of the charge generating layer is preferably a different resin to the binder resin of the charge transport layer. The charge generating layer and the charge transport layer of the multi-layer photosensitive member are typically formed in stated order. Therefore, the base resin of the charge generating layer preferably does not dissolve in a solvent used in an application liquid for forming the charge transport layer.

Preferable examples of the base resin contained in the charge generating layer include styrene-butadiene copolymers, styrene-acrylonitrile copolymers, styrene-maleate copolymers, acrylic copolymers, styrene-acrylate copolymers, polyethylene resins, ethylene-vinyl acetate copolymers, chlorinated polyethylene resins, polyvinyl chloride resins, polypropylene resins, ionomer resins, vinyl chloride-vinyl acetate copolymers, alkyd resins, polyamide resins, urethane resins, polysulfone resins, diallyl phthalate resins, ketone resins, polyvinyl acetal resins, polyvinyl butyral resins, polyether resins, silicone resins, epoxy resins, phenolic resins, urea resins, melamine resins, epoxy acrylate resins, and urethane-acrylate resins. A specific example of a preferable base resin that can be contained in the charge generating layer is polyvinyl butyral. Any one of the base resins listed above may be used or a combination of any two or more of the base resins listed above may be used.

(Binder Resin)

Preferable examples of binder resins that can be contained in the charge transport layer or the single-layer photosensitive layer include thermoplastic resins, thermosetting resins, and photocurable resins. Preferable examples of thermoplastic resins that can be contained in the charge transport layer or the single-layer photosensitive layer include polycarbonate resins, styrene-based resins, styrene-butadiene copolymers, styrene-acrylonitrile copolymers, styrene-maleate copolymers, styrene-acrylate copolymers, acrylic copolymers, polyethylene resins, ethylene-vinyl acetate copolymers, chlorinated polyethylene resins, polyvinyl chloride resins, polypropylene resins, ionomers, vinyl chloride-vinyl acetate copolymers, alkyd resins, polyamide resins, urethane resins, polyarylate resins, polysulfone resins, diallyl phthalate resins, ketone resins, polyvinyl butyral resins, polyether resins, and polyester resins. Preferable examples of thermosetting resins that can be contained in the charge transport layer or the single-layer photosensitive layer include silicone resins, epoxy resins, phenolic resins, urea resins, melamine resins, and cross-linking resins. Preferable examples of photocurable resins that can be contained in the charge transport layer or the single-layer photosensitive layer include epoxy acrylate resins and urethane-acrylate copolymers. Any one of the resins listed above may be used or a combination of any two or more of the resins listed above may be used.

In terms of molecular weight, the binder resin contained in the charge transport layer or the single-layer photosensitive layer preferably has a viscosity average molecular weight of at least 40,000, and more preferably at least 40,000 and no greater than 52,500. If the viscosity average molecular weight of the binder resin is too low, the binder resin may have insufficient abrasion resistance and as a consequence abrasion of the charge transport layer or the single-layer photosensitive layer in which the binder resin is contained may have a high tendency to occur. On the other hand, if the viscosity average molecular weight of the binder resin is too high, it may be difficult to cause the binder resin to dissolve in a solvent in order to form the charge transport layer or the single-layer photosensitive layer. Also, formation of the charge transport layer or the single-layer photosensitive layer is difficult if the application liquid used for formation thereof has excessively high viscosity.

[Additives]

Additives described below may be optionally contained in any one or more of the multi-layer photosensitive layer (charge generating layer and charge transport layer), the single-layer photosensitive layer, and an intermediate layer. Specific examples of additives that can be used include antidegradants (examples include antioxidants, radical scavengers, singlet quenchers, and ultraviolet absorbing agents), softeners, surface modifiers, extenders, thickeners, dispersion stabilizers, waxes, acceptors, donors, surfactants, plasticizers, sensitizers, and leveling agents. Examples of preferable antioxidants include hindered phenols, hindered amines, paraphenylenediamine, arylalkanes, 1,4-benzenediol, spirochromanes, spiroindanones, and derivatives of any of the above compounds. Further, an organosulfur compound or an organophosphorus compound may be used as an antioxidant.

[Intermediate Layer]

The photosensitive member according to the present embodiment may optionally include an intermediate layer (for example, an underlayer). In the single-layer photosensitive member, the intermediate layer may be present between the substrate and the single-layer photosensitive layer. In the multi-layer photosensitive member, the intermediate layer may be present between the substrate and the charge generating layer. The intermediate layer for example contains a resin and inorganic particles dispersed in the resin. Presence of the intermediate layer enables smooth flow of current generated during exposure of the photosensitive member to light (more specifically, current flowing from the surface of the photosensitive member to the charge generating layer), while also maintaining insulation sufficient to inhibit occurrence of leak current from the substrate of the photosensitive member to the surface of the photosensitive member.

Examples of inorganic particles that can be contained in the intermediate layer includes particles of metals (specific examples include aluminum, iron, and copper), particles of metal oxides (specific examples include titanium oxide, alumina, zirconium oxide, tin oxide, and zinc oxide), and particles of non-metal oxides (specific examples include silica). Any one type of inorganic particles listed above may be used or a combination of any two or more types of inorganic particles listed above may be used.

[Photosensitive Member Production Method]

The following explains an example of a production method for the single-layer photosensitive member. The single-layer photosensitive member is produced by applying an application liquid for single-layer photosensitive layer formation (referred to below as a first application liquid) onto the substrate and subsequently drying the applied liquid. The first application liquid can be prepared by dissolving or dispersing components of the single-layer photosensitive layer (for example, the charge generating material, the charge transport material, and the binder resin) in a solvent. The first application liquid may optionally contain one or more additives depending on necessity thereof.

The following explains an example of a production method for the multi-layer photosensitive member. An application liquid for charge generating layer formation (referred to below as a second application liquid) and an application liquid for charge transport layer formation (referred to below as a third application liquid) are each prepared. The second application liquid is applied onto the substrate and subsequently dried thereon to form the charge generating layer. After formation of the charge generating layer, the third application liquid is applied onto the charge generating layer and subsequently dried thereon to form the charge transport layer. The multi-layer photosensitive member is obtained as a result of the above process.

The second application liquid can be prepared by dissolving or dispersing components of the charge generating layer (for example, the charge generating material and the base resin) in a solvent. The third application liquid can be prepared by dissolving or dispersing components of the charge transport layer (for example, the charge transport material and the binder resin) in a solvent. Either or both of the second application liquid and the third application liquid may optionally contain one or more additives depending on necessity thereof.

Preferable examples of solvents that can be contained in the application liquids (first application liquid, second application liquid, and third application liquid) include alcohols (specific examples include methanol, ethanol, isopropanol, and butanol), aliphatic hydrocarbons (specific examples include n-hexane, octane, and cyclohexane), aromatic hydrocarbons (specific examples include benzene, toluene, and xylene), halogenated hydrocarbons (specific examples include dichloromethane, dichloroethane, tetrachloromethane, and chlorobenzene), ethers (specific examples include dimethyl ether, diethyl ether, tetrahydrofuran, ethylene glycol dimethyl ether, and diethylene glycol dimethyl ether), ketones (specific examples include acetone, methyl ethyl ketone, and cyclohexanone), esters (specific examples include ethyl acetate and methyl acetate), dimethyl formaldehyde, dimethyl formamide, and dimethyl sulfoxide. Any one of the solvents listed above may be used or a combination of any two or more of the solvents listed above may be used. In order to improve workability in production of the photosensitive member, a non-halogenated solvent is preferably used.

Mixing or dispersion of each of the application liquids can for example be performed using a bead mill, a roll mill, a ball mill, an attritor, a paint shaker, or an ultrasonic disperser. A surfactant may be added to the application liquid in order to improve dispersibility of each component contained in the application liquid.

Preferable examples of methods that can be used to apply the application liquid include dip coating, spray coating, spin coating, and bar coating.

Preferable examples of methods that can be used to dry the application liquid include heat treatment (hot-air drying) using a high-temperature dryer or a reduced pressure dryer. The heat treatment is for example preferably performed for at least 3 minutes and no greater than 120 minutes at a temperature of at least 40° C. and no greater than 150° C.

EXAMPLES

The following explains examples of the present disclosure. Note that the present disclosure is not in any way limited to the scope of the examples.

[Synthesis of Hydrazone Derivative of Triphenylamine Represented by Formula (HT-1)]

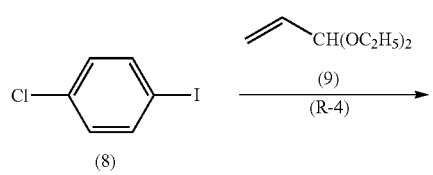

A reaction represented by chemical equation (R-4) shown above was carried out. More specifically, 11.9 g (0.05 mol) of a compound represented by formula (8) shown above, 100 mL of N,N-dimethylformamide, 22.9 mL (0.15 mol) of a compound represented by formula (9) shown above, 30 g (0.1 mol) of tetrabutylammonium acetate, 10.4 g (0.075 mol) of potassium carbonate, 3.7 g (0.05 mol) of potassium chloride, and 0.3 g (1.5 mmol) of palladium acetate were added into a two-necked flask have a capacity of 500 mL. Next, the flask contents were caused to react while being stirred for 3 hours at 90° C.

After reaction, aqueous hydrochloric acid was poured into the flask contents and toluene was also added to the flask contents to yield a liquid mixture. Next, an organic phase was extracted from the mixture using a separation funnel. The extracted organic phase was washed three times using ion exchanged water. Next, dehydration of the washed organic phase was performed using anhydrous sodium sulfate. After dehydration, solvent was evaporated from the organic phase to yield a residue.

Next, the residue was purified by silica gel column chromatography. In the silica gel column chromatography, a solvent obtained through mixing hexane and ethyl acetate in a mass ratio of 9:1 (hexane:ethyl acetate) was used as a developing solvent. As a result of the above process, 7.3 g of a compound represented by formula (10) shown above was obtained with a yield of 88% by mass.

Next, a reaction represented by chemical equation (R-5) shown above was carried out. More specifically, 16.2 g (0.09756 mol) of the compound represented by formula (10) shown above, 21.5 g (0.09756 mol) of a compound represented by formula (11) shown above, and 100 mL of toluene were added into a flask having a capacity of 200 mL that was equipped with a Dean-Stark trap. Next, the flask contents were caused to react while being stirred for 2 hours at 120° C. Activated clay was subsequently added into the flask. Next, after filtering the flask contents, toluene was evaporated under reduced pressure to yield a residue. The obtained residue was purified by silica gel column chromatography. In the silica gel column chromatography, a solvent obtained by mixing chloroform and hexane in a mass ratio of 9:1 (chloroform:hexane) was used as a developing solvent. As a result of the above process, 29.0 g of a compound represented by formula (12) shown above was obtained with a yield of 90% by mass.

Next, the residue was purified by silica gel column chromatography. In the silica gel column chromatography, a solvent obtained by mixing chloroform and hexane in a mass ratio of 9:1 (chloroform:hexane) was used as a developing solvent. As a result of the above process, 9.3 g of the hydrazone derivative of triphenylamine represented by formula (HT-1) was obtained with a yield of 89% by mass.

The $^1$H-NMR spectral chart illustrated in FIG. 1 was obtained by measuring a $^1$H-NMR spectrum (resonance frequency: 300 MHz) of the compound obtained through the above process. $CDCl_3$ was used as a solvent. The $^1$H-NMR spectral chart confirms that the compound obtained through

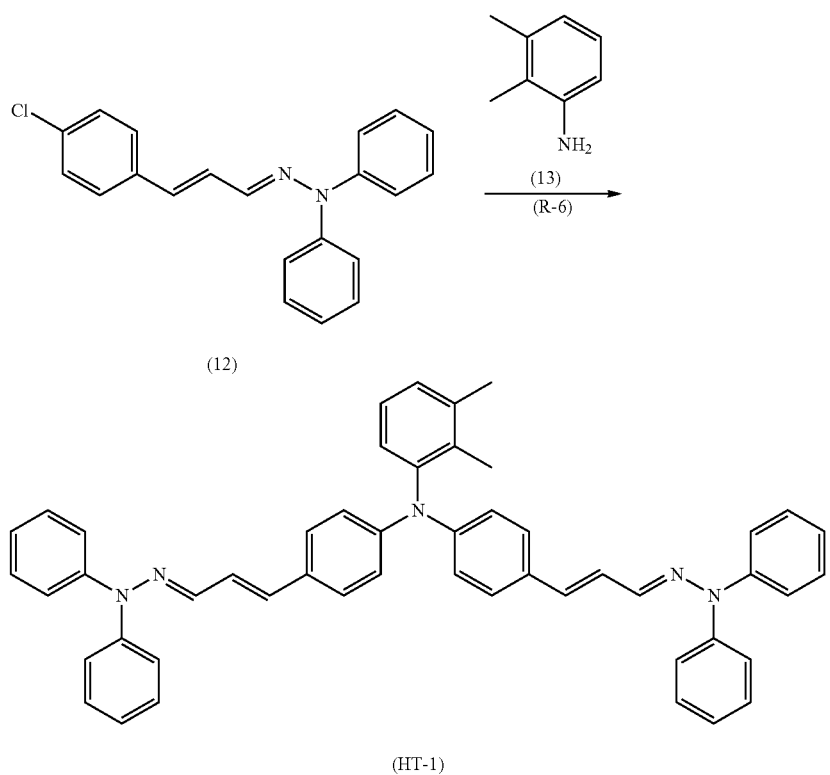

Next, a reaction represented by chemical equation (R-6) shown above was carried out. More specifically, 8.9 g (0.03 mol) of the compound represented by formula (12) shown above, 0.0662 g (0.000189 mol) of tricyclohexylphosphine, 0.0864 g (0.0000944 mol) of tris(dibenzylideneacetone)dipalladium, 5.3 g (0.06 mol) of sodium tert-butoxide (t-BuONa), and 1.8 g (0.015 mol) of a compound represented by formula (13) shown above were added into a three-necked flask. Next, 500 ml of distilled o-xylene was added into the flask. Air in the flask was subsequently displaced with argon gas and the flask contents were caused to react while stirring for 5 hours at 120° C.

After reaction, the flask contents were cooled to room temperature to yield an organic phase in the flask. The obtained organic phase was washed three times using ion exchanged water. Next, dehydration treatment using anhydrous sodium sulfate and absorption treatment using activated clay were performed on the washed organic phase. After the dehydration and absorption treatment, o-xylene was evaporated from the organic phase under reduced pressure to yield a residue.

the above process was the hydrazone derivative of triphenylamine represented by formula (HT-1).

[Synthesis of Hydrazone Derivative of Triphenylamine Represented by Formula (HT-2)]

Figure 2:
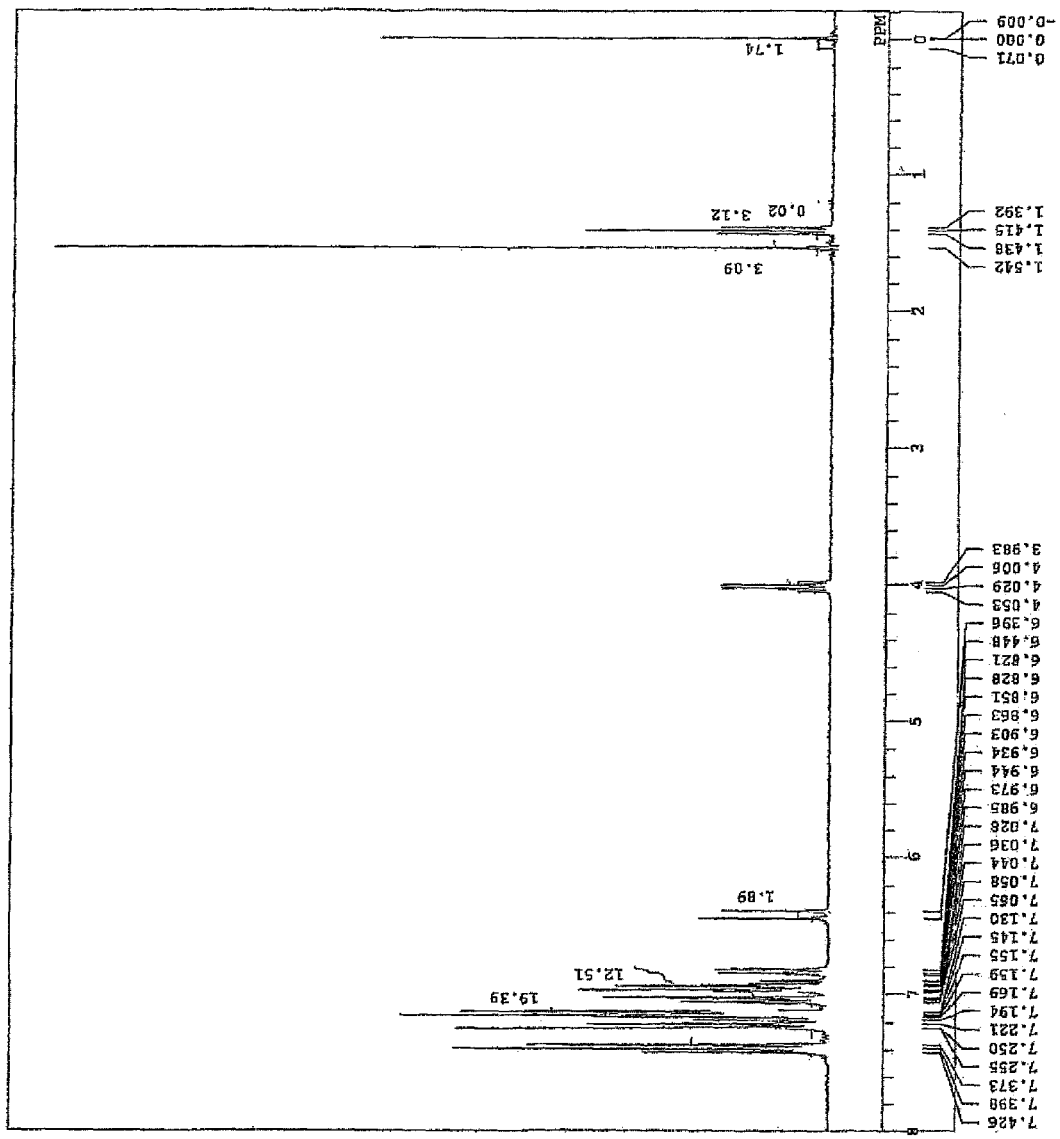
FIG. 2 is a $^1$H-NMR spectral chart for a hydrazone derivative of triphenylamine represented by formula (HT-2).

The hydrazone derivative of triphenylamine represented by formula (HT-2) was synthesized by, with respect to the method described above for synthesis of the hydrazone derivative of triphenylamine represented by formula (HT-1), using a compound represented by formula (14) shown below instead of the compound represented by formula (13) shown above in order to carry out a reaction represented by chemical equation (R-7) shown below instead of the reaction represented by chemical equation (R-6) shown above. As a result of the above process, the hydrazone derivative of triphenylamine represented by formula (HT-2) was obtained with a yield of 85% by mass. FIG. 2 is a $^1$H-NMR spectral chart for the hydrazone derivative of triphenylamine represented by formula (HT-2).

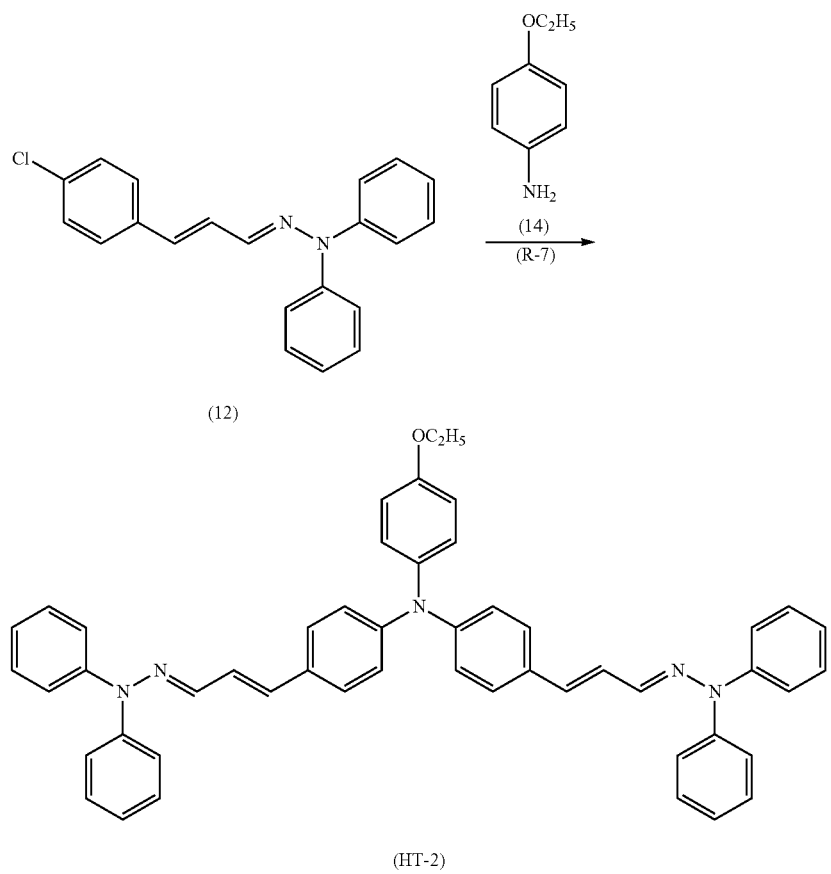

(HT-2)

Note that in synthesis of the hydrazone derivative of triphenylamine represented by formula (HT-2), and also in synthesis of the hydrazone derivatives of triphenylamine represented by formulae (HT-3) to (HT-7) described below, additive amounts of materials were adjusted in order that a mixing ratio (molar ratio) of the materials was the same as a mixing ratio (molar ratio) of materials in synthesis of the hydrazone derivative of triphenylamine represented by formula (HT-1).

[Synthesis of Hydrazone Derivative of Triphenylamine Represented by Formula (HT-3)]

Figure 3:
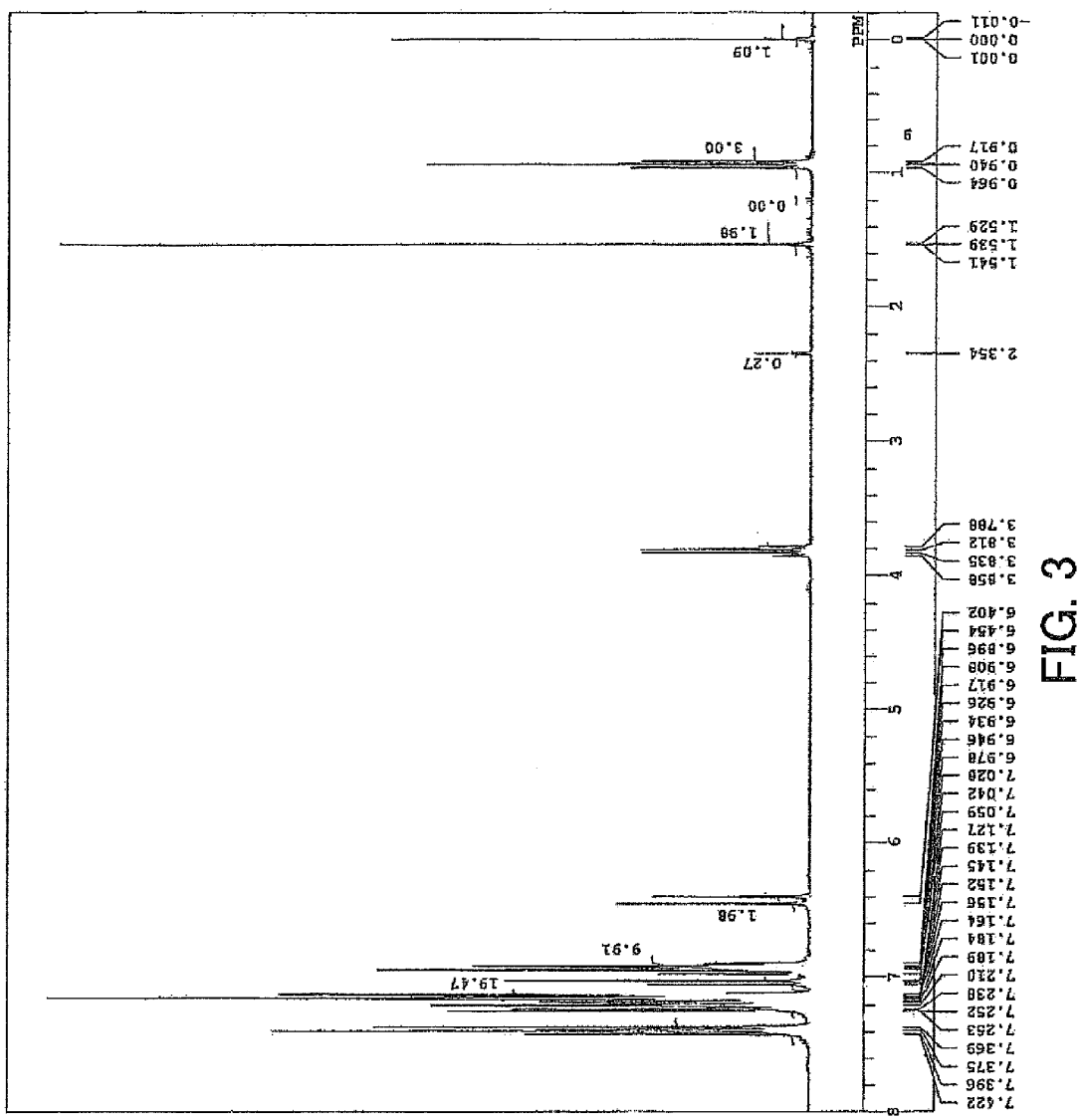
FIG. 3 is a $^1$H-NMR spectral chart for a hydrazone derivative of triphenylamine represented by formula (HT-3).

The hydrazone derivative of triphenylamine represented by formula (HT-3) was synthesized by, with respect to the method described above for synthesis of the hydrazone derivative of triphenylamine represented by formula (HT-1), using a compound represented by formula (15) shown below instead of the compound represented by formula (13) shown above in order to carry out a reaction represented by chemical equation (R-8) shown below instead of the reaction represented by chemical equation (R-6) shown above. As a result of the above process, the hydrazone derivative of triphenylamine represented by formula (HT-3) was obtained with a yield of 75% by mass. FIG. 3 is a $^1$H-NMR spectral chart for the hydrazone derivative of triphenylamine represented by formula (HT-3).

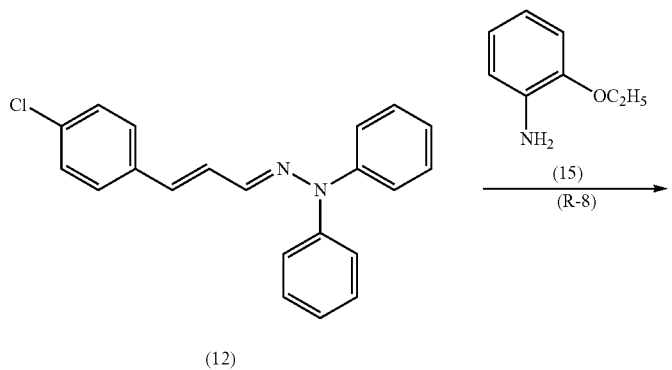

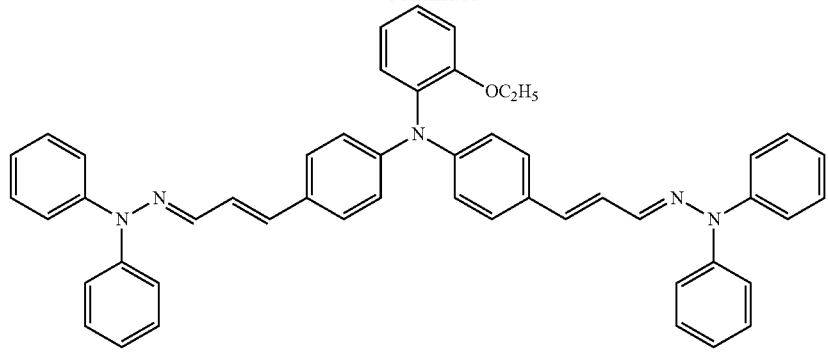

(HT-3)

[Synthesis of Hydrazone Derivative of Triphenylamine Represented by Formula (HT-4)]

Figure 4:
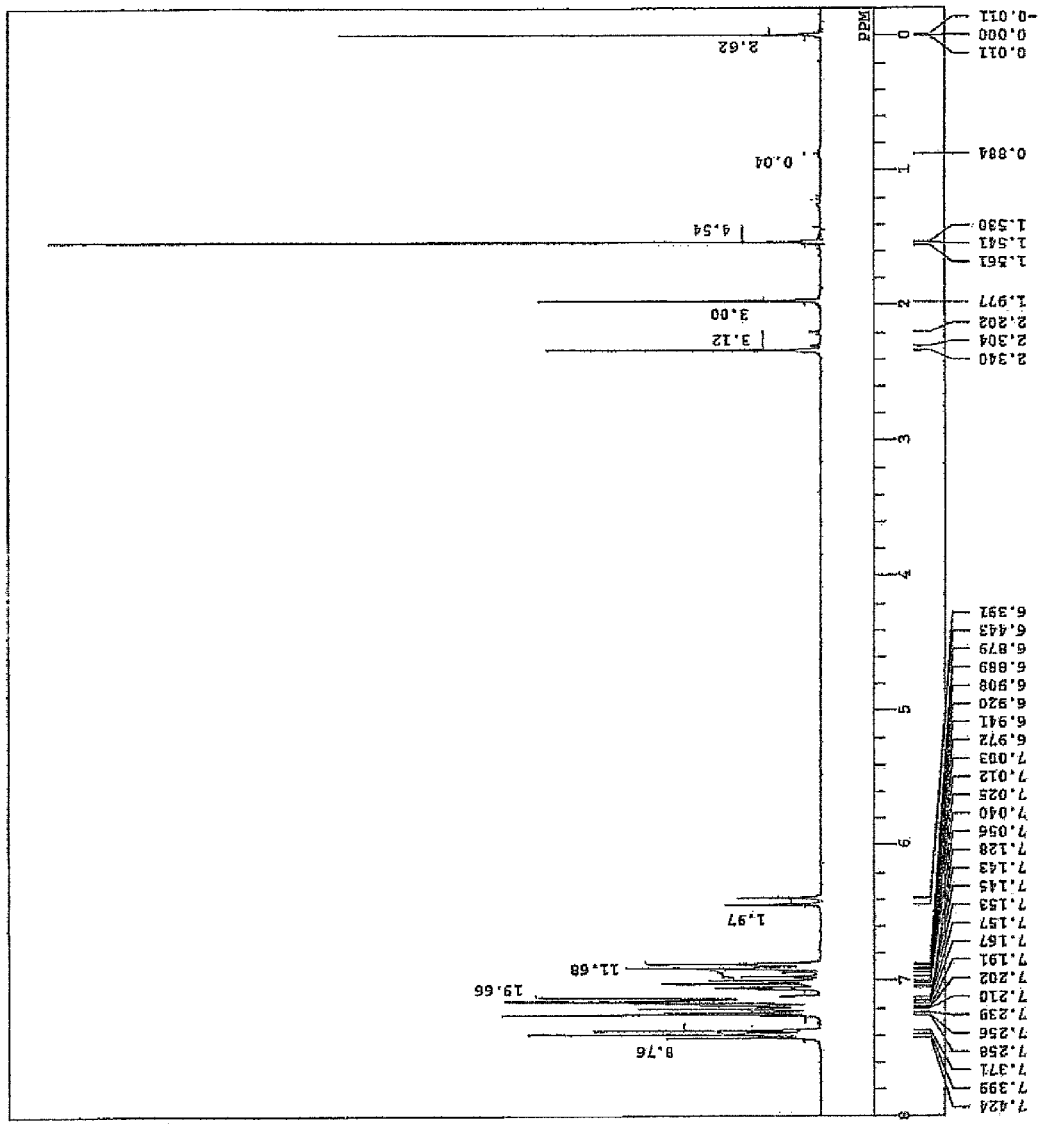
FIG. 4 is a $^1$H-NMR spectral chart for a hydrazone derivative of triphenylamine represented by formula (HT-4).

The hydrazone derivative of triphenylamine represented by formula (HT-4) was synthesized by, with respect to the method described above for synthesis of the hydrazone derivative of triphenylamine represented by formula (HT-1), using a compound represented by formula (16) shown below instead of the compound represented by formula (13) shown above in order to carry out a reaction represented by chemical equation (R-9) shown below instead of the reaction represented by chemical equation (R-6) shown above. As a result of the above process, the hydrazone derivative of triphenylamine represented by formula (HT-4) was obtained with a yield of 80% by mass. FIG. 4 is a $^1$H-NMR spectral chart for the hydrazone derivative of triphenylamine represented by formula (HT-4).

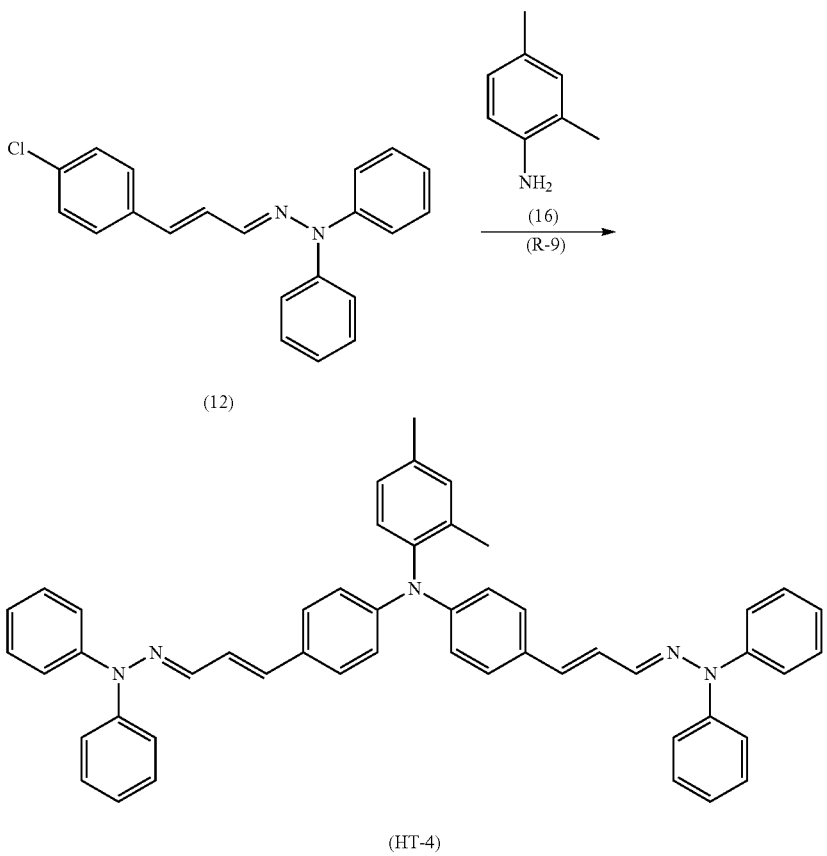

[Synthesis of Hydrazone Derivative of Triphenylamine Represented by Formula (HT-5)]

The hydrazone derivative of triphenylamine represented by formula (HT-5) was synthesized by, with respect to the method described above for synthesis of the hydrazone derivative of triphenylamine represented by formula (HT-1), using a compound represented by formula (17) shown below instead of the compound represented by formula (13) shown above in order to carry out a reaction represented by chemical equation (R-10) shown below instead of the reaction represented by chemical equation (R-6) shown above. As a result of the above process, the hydrazone derivative of triphenylamine represented by formula (HT-5) was obtained with a yield of 80% by mass.

method described above for synthesis of the hydrazone derivative of triphenylamine represented by formula (HT-1), using a compound represented by formula (18) shown below instead of the compound represented by formula (13) shown above in order to carry out a reaction represented by chemical equation (R-11) shown below instead of the reac-

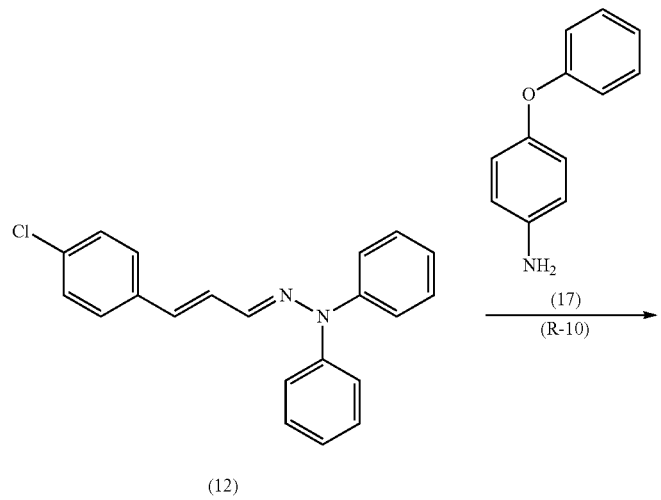

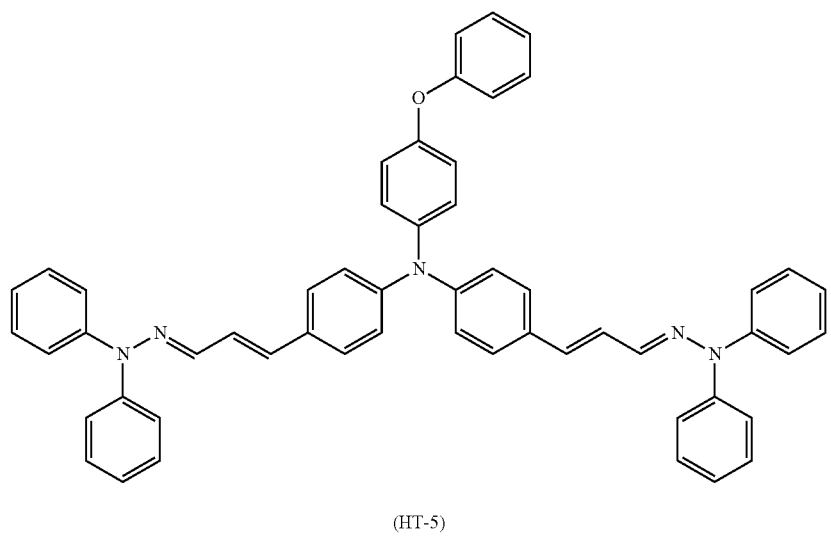

(HT-5)

[Synthesis of Hydrazone Derivative of Triphenylamine Represented by Formula (HT-6)]

The hydrazone derivative of triphenylamine represented by formula (HT-6) was synthesized by, with respect to the tion represented by chemical equation (R-6) shown above. As a result of the above process, the hydrazone derivative of triphenylamine represented by formula (HT-6) was obtained with a yield of 70% by mass.

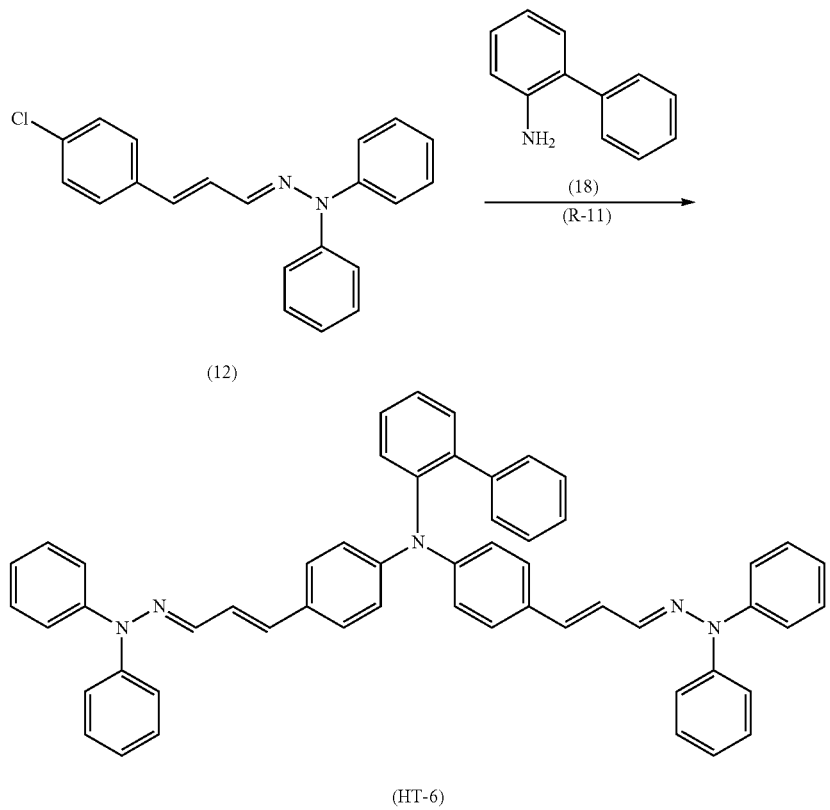 [SMILES: Clc1ccc(/C=C/C=N/N(c2ccccc2)c2ccccc2)cc1 ; Nc1ccccc1-c1ccccc1 ; "(R-11)" ; C(=C\c1ccc(N(c2ccc(/C=C/C=N/N(c3ccccc3)c3ccccc3)cc2)c2ccccc2-c2ccccc2)cc1)/C=N/N(c1ccccc1)c1ccccc1 ; "(HT-6)"]

(HT-6)

[Synthesis of Hydrazone Derivative of Triphenylamine Represented by Formula (HT-7)]

The hydrazone derivative of triphenylamine represented by formula (HT-7) was synthesized by, with respect to the method described above for synthesis of the hydrazone derivative of triphenylamine represented by formula (HT-1), using a compound represented by formula (19) shown below instead of the compound represented by formula (10) shown above in order to carry out a reaction represented by chemical equation (R-12) shown below instead of the reaction represented by chemical equation (R-5) shown above. As a result of the above process, a compound represented by formula (20) was obtained with a yield of 90% by mass.

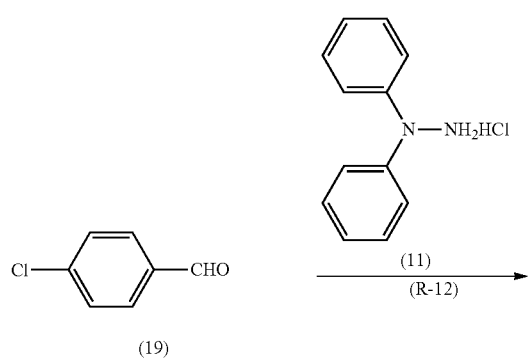

-continued

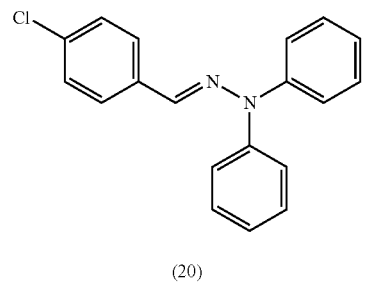

(20)

Also, in synthesis of the hydrazone derivative of triphenylamine represented by formula (HT-7), with respect to the method described above for synthesis of the hydrazone derivative of triphenylamine represented by formula (HT-2), the compound represented by formula (20) shown above was used instead of the compound represented by formula (12) shown above in order to carry out a reaction represented by chemical equation (R-13) shown below instead of the reaction represented by chemical equation (R-7) shown above. As a result of the above process, the hydrazone derivative of triphenylamine represented by formula (HT-7) was obtained with a yield of 85% by mass.

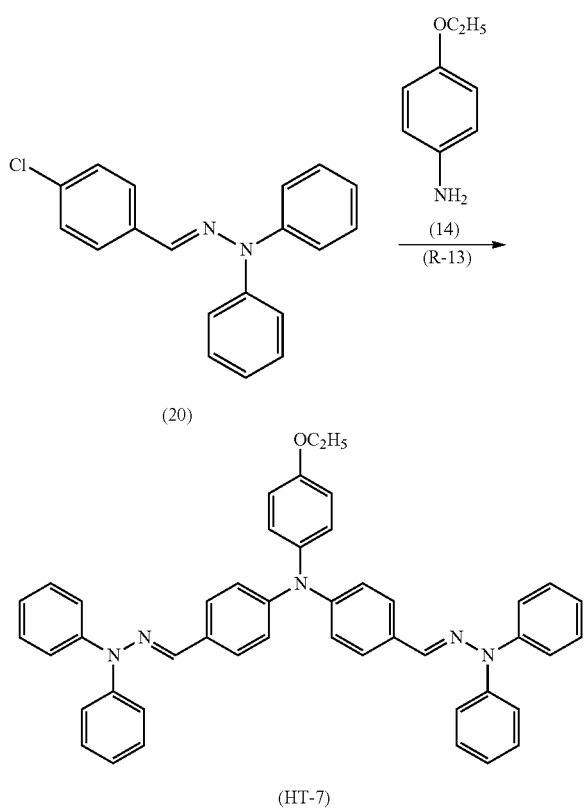 [SMILES: Clc1ccc(/C=N/N(c2ccccc2)c2ccccc2)cc1 ; CCOc1ccc(N)cc1 ; "(R-13)" ; CCOc1ccc(N(c2ccc(/C=N/N(c3ccccc3)c3ccccc3)cc2)c2ccc(/C=N/N(c3ccccc3)c3ccccc3)cc2)cc1 ; "(HT-7)"]

[Production of Photosensitive Member A-1]
(Intermediate Layer Formation)

First, surface treated titanium oxide particles (test sample SMT-02 produced by Tayca Corporation, number average primary particle size 10 nm) were prepared. More specifically, titanium oxide particles were surface treated using alumina and silica and were also subsequently surface treated using methyl hydrogen polysiloxane while being subjected to wet dispersion using a bead mill. The above process yielded titanium oxide particles for use in intermediate layer formation.

Next, 2.8 parts by mass of the titanium oxide particles prepared as described above and 1 part by mass of copolyamide resin (DAIAMID X4685 produced by Daicel-Evonik Ltd.) were added to a solvent of 10 parts by mass of ethanol and 2 parts by mass of butanol. The materials were mixed in the solvent for 5 hours using a bead mill to disperse the materials in the solvent. The above process yielded an application liquid for intermediate layer formation.

Next, the application liquid that was obtained was filtered using a filter having a pore size of 5 μm. The filtered application liquid was applied onto the surface of an aluminum drum-shaped support (diameter 30 mm, length 238.5 mm) by dip coating. After application, the application liquid was dried for 30 minutes at 130° C. Through the above process, an intermediate layer having a thickness of 1.5 μm was formed on a substrate (drum-shaped support).

(Charge Generating Layer Formation)

First, 1 part by mass of Y-form titanyl phthalocyanine (Y-TiOPc) and 1 part by mass of polyvinyl butyral resin (Denka Butyral 6000EP produced by Denki Kagaku Kogyo Kabushiki Kaisha) were added to a solvent of 40 parts by mass of propylene glycol monomethyl ether and 40 parts by mass of tetrahydrofuran. Next, the materials were mixed in the solvent for 2 hours using a bead mill to disperse the materials in the solvent. The above process yielded an application liquid for charge generating layer formation.

Next, the application liquid that was obtained was filtered using a filter having a pore size of 3 μm. The filtered application liquid was applied by dip coating onto the intermediate layer formed as described above. After application, the application liquid was dried for 5 minutes at 50° C. Through the above process, a charge generating layer having a thickness of 0.3 μm was formed on the intermediate layer.

(Charge Transport Layer Formation)

First, 70 parts by mass of the hydrazone derivative of triphenylamine represented by formula (HT-1), 5 parts by mass of BHT (2,6-di-tert-butyl-p-cresol), and 100 parts by mass of Z-form polycarbonate resin (Panlite (registered Japanese trademark) TS-2050 produced by Teijin Limited, viscosity average molecular weight 50,000) were added to a solvent of 430 parts by mass of tetrahydrofuran and 430 parts by mass of toluene. Next, the materials were mixed in the solvent for 12 hours using a circulating ultrasonic disperser to disperse the materials in the solvent. The above process yielded an application liquid for charge transport layer formation.

Next, the application liquid that was obtained was filtered using a filter having a pore size of 3 μm. The filtered application liquid was applied by dip coating onto the charge generating layer formed as described above. After application, the application liquid was dried for 30 minutes at 130° C. Through the above process, a charge transport layer having a thickness of 20 μm was formed on the charge generating layer. The photosensitive member A-1 (multilayer photosensitive member) was obtained as a result of the process described above. In the photosensitive member A-1, the intermediate layer, the charge generating layer, and the charge transport layer were stacked in stated order on the substrate.

[Production of Photosensitive Member A-2]

A photosensitive member A-2 was produced according to the same production method as the photosensitive member A-1 in all aspects other than that the hydrazone derivative of triphenylamine represented by formula (HT-2) was used as a hole transport material instead of the hydrazone derivative of triphenylamine represented by formula (HT-1).

[Production of Photosensitive Member A-3]

A photosensitive member A-3 was produced according to the same production method as the photosensitive member A-1 in all aspects other than that the hydrazone derivative of triphenylamine represented by formula (HT-3) was used as a hole transport material instead of the hydrazone derivative of triphenylamine represented by formula (HT-1).

[Production of Photosensitive Member A-4]

A photosensitive member A-4 was produced according to the same production method as the photosensitive member A-1 in all aspects other than that the hydrazone derivative of triphenylamine represented by formula (HT-4) was used as a hole transport material instead of the hydrazone derivative of triphenylamine represented by formula (HT-1).

[Production of Photosensitive Member A-5]

A photosensitive member A-5 was produced according to the same production method as the photosensitive member A-1 in all aspects other than that the hydrazone derivative of triphenylamine represented by formula (HT-5) was used as a hole transport material instead of the hydrazone derivative of triphenylamine represented by formula (HT-1).

[Production of Photosensitive Member A-6]

A photosensitive member A-6 was produced according to the same production method as the photosensitive member A-1 in all aspects other than that the hydrazone derivative of triphenylamine represented by formula (HT-6) was used as a hole transport material instead of the hydrazone derivative of triphenylamine represented by formula (HT-1).

[Production of Photosensitive Member A-7]

A photosensitive member A-7 was produced according to the same production method as the photosensitive member A-1 in all aspects other than that the hydrazone derivative of triphenylamine represented by formula (HT-7) was used as a hole transport material instead of the hydrazone derivative of triphenylamine represented by formula (HT-1).

[Production of Photosensitive Member B-1]

A photosensitive member B-1 was produced according to the same production method as the photosensitive member A-1 in all aspects other than that a compound represented by formula (HT-A) shown below was used as a hole transport material instead of the hydrazone derivative of triphenylamine represented by formula (HT-1).

Next, the application liquid that was obtained was applied onto a conductive substrate by dip coating. The conductive substrate was an aluminum drum-shaped support (diameter 30 mm, length 238.5 mm) The application liquid was applied onto the conductive substrate through dip coating by immersing the conductive substrate in the application liquid at a speed of 5 mm/s.

Next, the applied application liquid (applied film) was heated for 30 minutes at 100° C. to remove tetrahydrofuran from the applied film. As a result of the above process, the photosensitive member A-8 including the conductive substrate and a single-layer photosensitive layer having a thickness of 25 µm located directly on the conductive substrate was obtained.

[Production of Photosensitive Member A-9]

A photosensitive member A-9 was produced according to the same production method as the photosensitive member A-8 in all aspects other than that an electron acceptor compound represented by formula (ET-2) shown below was used instead of the electron acceptor compound represented by formula (ET-1) shown above.

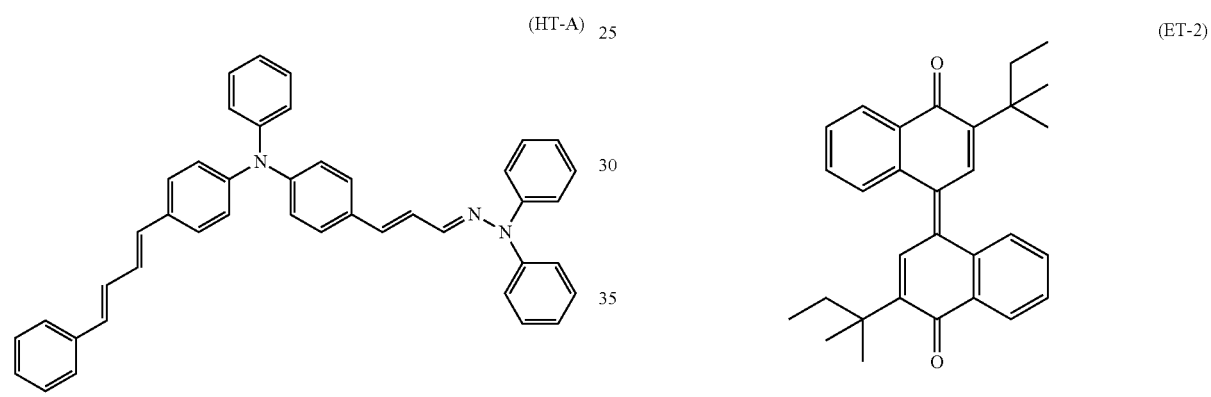

[Production of Photosensitive Member A-8]

First, 5 parts by mass of X-form metal-free phthalocyanine (x-H$_2$Pc), 80 parts by mass of the hydrazone derivative of triphenylamine represented by formula (HT-1), 50 parts by mass of an electron acceptor compound represented by formula (ET-1) shown below, 100 parts by mass of polycarbonate resin (Panlite (registered Japanese trademark) produced by Teijin Limited), and 800 parts by mass of tetrahydrofuran were added into a container of a ball mill. The contents of the container were then mixed for 50 hours using the ball mill to disperse the materials in the tetrahydrofuran. As a result of the above process, an application liquid for single-layer photosensitive layer formation was obtained.

[Production of Photosensitive Member A-10]

A photosensitive member A-10 was produced according to the same production method as the photosensitive member A-9 in all aspects other than that Y-form titanyl phthalocyanine (Y-TiOPc) was used as a charge generating material instead of X-form metal-free phthalocyanine (x-H$_2$Pc).

[Production of Photosensitive Member A-11]

A photosensitive member A-11 was produced according to the same production method as the photosensitive member A-8 in all aspects other than that the hydrazone derivative of triphenylamine represented by formula (HT-2) was used as a hole transport material instead of the hydrazone derivative of triphenylamine represented by formula (HT-1).

[Production of Photosensitive Member A-12]

A photosensitive member A-12 was produced according to the same production method as the photosensitive member A-11 in all aspects other than that the electron acceptor compound represented by formula (ET-2) was used instead of the electron acceptor compound represented by formula (ET-1).

[Production of Photosensitive Member A-13]

A photosensitive member A-13 was produced according to the same production method as the photosensitive member A-12 in all aspects other than that Y-form titanyl phthalocyanine (Y-TiOPc) was used as a charge generating material instead of X-form metal-free phthalocyanine (x-H$_2$Pc).

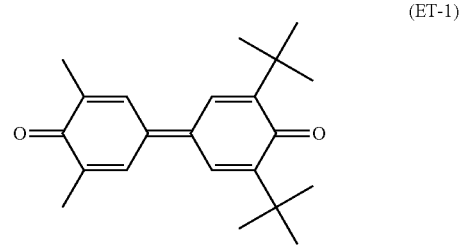 [SMILES: CC1=CC(=C2C=C(C(C)(C)C)C(=O)C(C(C)(C)C)=C2)C=C(C)C1=O]

[Production of Photosensitive Member A-14]

A photosensitive member A-14 was produced according to the same production method as the photosensitive member A-8 in all aspects other than that the hydrazone derivative of triphenylamine represented by formula (HT-3) was used as a hole transport material instead of the hydrazone derivative of triphenylamine represented by formula (HT-1).

[Production of Photosensitive Member A-15]

A photosensitive member A-15 was produced according to the same production method as the photosensitive member A-14 in all aspects other than that the electron acceptor compound represented by formula (ET-2) was used instead of the electron acceptor compound represented by formula (ET-1).

[Production of Photosensitive Member A-16]

A photosensitive member A-16 was produced according to the same production method as the photosensitive member A-15 in all aspects other than that Y-form titanyl phthalocyanine (Y-TiOPc) was used as a charge generating material instead of X-form metal-free phthalocyanine (x-$H_2$Pc).

[Production of Photosensitive Member A-17]

A photosensitive member A-17 was produced according to the same production method as the photosensitive member A-8 in all aspects other than that the hydrazone derivative of triphenylamine represented by formula (HT-4) was used as a hole transport material instead of the hydrazone derivative of triphenylamine represented by formula (HT-1).

[Production of Photosensitive Member A-18]

A photosensitive member A-18 was produced according to the same production method as the photosensitive member A-17 in all aspects other than that the electron acceptor compound represented by formula (ET-2) was used instead of the electron acceptor compound represented by formula (ET-1).

[Production of Photosensitive Member A-19]

A photosensitive member A-19 was produced according to the same production method as the photosensitive member A-18 in all aspects other than that Y-form titanyl phthalocyanine (Y-TiOPc) was used as a charge generating material instead of X-form metal-free phthalocyanine (x-$H_2$Pc).

[Production of Photosensitive Member A-20]

A photosensitive member A-20 was produced according to the same production method as the photosensitive member A-8 in all aspects other than that the hydrazone derivative of triphenylamine represented by formula (HT-5) was used as a hole transport material instead of the hydrazone derivative of triphenylamine represented by formula (HT-1).

[Production of Photosensitive Member A-21]

A photosensitive member A-21 was produced according to the same production method as the photosensitive member A-20 in all aspects other than that the electron acceptor compound represented by formula (ET-2) was used instead of the electron acceptor compound represented by formula (ET-1).

[Production of Photosensitive Member A-22]

A photosensitive member A-22 was produced according to the same production method as the photosensitive member A-21 in all aspects other than that Y-form titanyl phthalocyanine (Y-TiOPc) was used as a charge generating material instead of X-form metal-free phthalocyanine (x-$H_2$Pc).

[Production of Photosensitive Member A-23]

A photosensitive member A-23 was produced according to the same production method as the photosensitive member A-8 in all aspects other than that the hydrazone derivative of triphenylamine represented by formula (HT-6) was used as a hole transport material instead of the hydrazone derivative of triphenylamine represented by formula (HT-1).

[Production of Photosensitive Member A-24]

A photosensitive member A-24 was produced according to the same production method as the photosensitive member A-23 in all aspects other than that the electron acceptor compound represented by formula (ET-2) was used instead of the electron acceptor compound represented by formula (ET-1).

[Production of Photosensitive Member A-25]

A photosensitive member A-25 was produced according to the same production method as the photosensitive member A-24 in all aspects other than that Y-form titanyl phthalocyanine (Y-TiOPc) was used as a charge generating material instead of X-form metal-free phthalocyanine (x-$H_2$Pc).

[Production of Photosensitive Member A-26]

A photosensitive member A-26 was produced according to the same production method as the photosensitive member A-8 in all aspects other than that the hydrazone derivative of triphenylamine represented by formula (HT-7) was used as a hole transport material instead of the hydrazone derivative of triphenylamine represented by formula (HT-1).

[Production of Photosensitive Member A-27]

A photosensitive member A-27 was produced according to the same production method as the photosensitive member A-26 in all aspects other than that the electron acceptor compound represented by formula (ET-2) was used instead of the electron acceptor compound represented by formula (ET-1).

[Production of Photosensitive Member A-28]

A photosensitive member A-28 was produced according to the same production method as the photosensitive member A-27 in all aspects other than that Y-form titanyl phthalocyanine (Y-TiOPc) was used as the charge generating material instead of X-form metal-free phthalocyanine (x-$H_2$Pc).

[Production of Photosensitive Member B-2]

A photosensitive member B-2 was produced according to the same production method as the photosensitive member A-8 in all aspects other than that the hydrazone derivative of triphenylamine represented by formula (HT-A) was used as a hole transport material instead of the hydrazone derivative of triphenylamine represented by formula (HT-1).

[Production of Photosensitive Member B-3]

A photosensitive member B-3 was produced according to the same production method as the photosensitive member B-2 in all aspects other than that the electron acceptor compound represented by formula (ET-2) was used instead of the electron acceptor compound represented by formula (ET-1).

[Production of Photosensitive Member B-4]

A photosensitive member B-4 was produced according to the same production method as the photosensitive member B-3 in all aspects other than that Y-form titanyl phthalocyanine (Y-TiOPc) was used as a charge generating material instead of X-form metal-free phthalocyanine (x-$H_2$Pc).

[Evaluation Method]

The following explains a method by which the samples (photosensitive members A-1 to A-28 and B-1 to B-4) were evaluated.

(Electrical Properties of Multi-Layer Photosensitive Members)

Electrical properties of each of the multi-layer photosensitive members (photosensitive members A-1 to A-7 and B-1) were evaluated according to the following procedure.

The sample (photosensitive member) was charged using a drum sensitivity test device (product of Gen-Tech, Inc.) under conditions of an initial charge of −700 V and a rotational speed of 31 rpm. Next, the surface of the sample was irradiated for 1.5 seconds with monochromatic light (wavelength 780 nm, half-width 20 nm, light intensity 0.4 µJ/cm$^2$) that was isolated from light emitted by a halogen lamp using a band pass filter. The surface potential (residual potential $V_L$) of the sample was measured 0.5 seconds after completion of irradiation with the monochromatic light. Measurement was performed under ambient conditions of 23° C. and 50% relative humidity.

(Electrical Properties of Single-Layer Photosensitive Members)

Electrical properties of each of the single-layer photosensitive members (photosensitive members A-8 to A-28 and B-2 to B-4) were measured according to the following procedure. The sample (single-layer photosensitive member) was charged using a drum sensitivity test device (product of Gen-Tech, Inc.) such that the surface potential of the sample was approximately +700 V. The surface potential of the sample once charged was measured as an initial surface potential $V_0$.

Next, the surface of the sample was irradiated for 1.5 seconds with monochromatic light (wavelength 780 nm, half-width 20 nm, light intensity 1.5 µJ/cm$^2$) that was isolated from light emitted by a halogen lamp using a band pass filter. The surface potential (residual potential $V_L$) of the sample was measured 0.5 seconds after completion of irradiation with the monochromatic light. Measurement was performed under ambient conditions of 23° C. and 50% relative humidity.

(External Appearance of Photosensitive Members)

The entire surface region of each sample (photosensitive member) was observed using an optical microscope in order to confirm whether or not a crystallized portion was present at the surface of the sample (photosensitive member). The external appearance of the photosensitive member observed as described above was evaluated in accordance with the following standard.

Good: No crystallized portion observed

Poor: Crystallized portion observed

[Evaluation Results]

Results of evaluation of the photosensitive members A-1 to A-28 and B-1 to B-4 are shown in Tables 1 and 2.

TABLE 1

| Photosensitive member | Hole transport material | Electrical properties $V_0$ [V] | $V_L$ [V] | Evaluation of external appearance (presence of crystallization) |
|---|---|---|---|---|
| A-1 | HT-1 | −700 | −106 | Good |
| A-2 | HT-2 | −700 | −108 | Good |
| A-3 | HT-3 | −700 | −110 | Good |
| A-4 | HT-4 | −700 | −111 | Good |
| A-5 | HT-5 | −700 | −108 | Good |
| A-6 | HT-6 | −700 | −114 | Good |
| A-7 | HT-7 | −700 | −115 | Good |
| B-1 | HT-A | −700 | −120 | Poor |

TABLE 2

| Photosensitive member | Charge generating material | Charge transport material — Hole transport material | Charge transport material — Electron transport material | Electrical properties $V_0$ [V] | $V_L$ [V] | Evaluation of external appearance (presence of crystallization) |
|---|---|---|---|---|---|---|
| A-8 | x-H$_2$Pc | HT-1 | ET-1 | +698 | +99 | Good |
| A-9 | x-H$_2$Pc | HT-1 | ET-2 | +700 | +100 | Good |
| A-10 | Y-TiOPc | HT-1 | ET-2 | +700 | +95 | Good |
| A-11 | x-H$_2$Pc | HT-2 | ET-1 | +700 | +101 | Good |
| A-12 | x-H$_2$Pc | HT-2 | ET-2 | +699 | +100 | Good |
| A-13 | Y-TiOPc | HT-2 | ET-2 | +699 | +96 | Good |
| A-14 | x-H$_2$Pc | HT-3 | ET-1 | +700 | +105 | Good |
| A-15 | x-H$_2$Pc | HT-3 | ET-2 | +699 | +105 | Good |
| A-16 | Y-TiOPc | HT-3 | ET-2 | +700 | +101 | Good |
| A-17 | x-H$_2$Pc | HT-4 | ET-1 | +700 | +106 | Good |
| A-18 | x-H$_2$Pc | HT-4 | ET-2 | +699 | +108 | Good |
| A-19 | Y-TiOPc | HT-4 | ET-2 | +700 | +102 | Good |
| A-20 | x-H$_2$Pc | HT-5 | ET-1 | +700 | +100 | Good |
| A-21 | x-H$_2$Pc | HT-5 | ET-2 | +699 | +102 | Good |
| A-22 | Y-TiOPc | HT-5 | ET-2 | +700 | +97 | Good |
| A-23 | x-H$_2$Pc | HT-6 | ET-1 | +700 | +108 | Good |
| A-24 | x-H$_2$Pc | HT-6 | ET-2 | +699 | +107 | Good |
| A-25 | Y-TiOPc | HT-6 | ET-2 | +700 | +104 | Good |
| A-26 | x-H$_2$Pc | HT-7 | ET-1 | +700 | +107 | Good |
| A-27 | x-H$_2$Pc | HT-7 | ET-2 | +699 | +109 | Good |
| A-28 | Y-TiOPc | HT-7 | ET-2 | +700 | +104 | Good |
| B-2 | x-H$_2$Pc | HT-A | ET-1 | +699 | +110 | Poor |
| B-3 | x-H$_2$Pc | HT-A | ET-2 | +700 | +107 | Poor |
| B-4 | Y-TiOPc | HT-A | ET-2 | +701 | +104 | Poor |

The photosensitive members A-1 to A-28 (photosensitive members according to Examples 1 to 28) each contained the hydrazone derivative of triphenylamine represented by general formula (1) as a charge transport material. As shown in Tables 1 and 2, residual potential was low and crystallization in the photosensitive layer was inhibited in each of the photosensitive members in which the hydrazone derivative of triphenylamine represented by general formula (1) was used. Thus, the photosensitive members according to Examples 1 to 28 had excellent electrical properties and surface appearance.

What is claimed is:

1. A hydrazone derivative of triphenylamine represented by general formula (1)

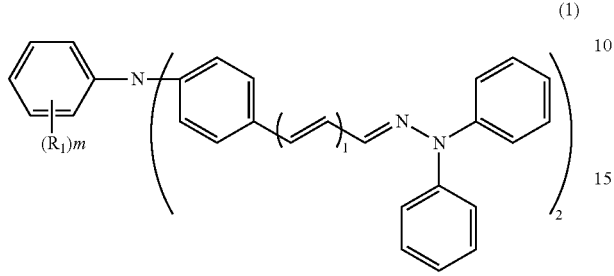

where, in the general formula (1), $R_1$ represents at least one chemical group selected from the group consisting of an ethoxy group, a phenoxy group, and a phenyl group, m represents 1, and l represents 1.

2. The hydrazone derivative of triphenylamine according to claim 1, wherein
in the general formula (1), $R_1$ represents an ethoxy group.

3. The hydrazone derivative of triphenylamine according to claim 2, wherein
the chemical group represented by $R_1$ in the general formula (1) is at an ortho or para substitution position.

4. The hydrazone derivative of triphenylamine according to claim 1, wherein
in the general formula (1), $R_1$ represents a phenoxy group.

5. The hydrazone derivative of triphenylamine according to claim 1, wherein
in the general formula (1), $R_1$ represents a phenyl group.

6. An electrophotographic photosensitive member comprising
a photosensitive layer containing a charge generating material, a charge transport material, and a binder resin, wherein
the photosensitive layer is either one of:
a multi-layer photosensitive layer including a charge generating layer that contains the charge generating material and a charge transport layer that contains the charge transport material and the binder resin, and in which the charge generating layer and the charge transport layer are stacked with the charge transport layer as an uppermost layer; and
a single-layer photosensitive layer containing the charge generating material, the charge transport material, and the binder resin, and
the charge transport material contained in the photosensitive layer is the hydrazone derivative of triphenylamine according to claim 1.

7. The electophotographic photosensitive member according to claim 6, wherein
the photosensitive layer contains the hydrazone derivative of triphenylamine according to claim 1 as a hole transport material, and
the photosensitive layer further contains a charge transport material that is an electron transport material.

* * * * *